United States Patent
Izvarina

(10) Patent No.: US 11,363,981 B2
(45) Date of Patent: Jun. 21, 2022

(54) METHODS AND SYSTEMS FOR THERAPEUTIC NEUROMODULATION

(71) Applicant: Biosensor, Inc., Madison, CT (US)

(72) Inventor: Natalia Izvarina, Saint Petersburg (RU)

(73) Assignee: Bionsensor, Inc., Madison, CT (US)

(*) Notice: Subject to any disclaimer, the term of this patent is extended or adjusted under 35 U.S.C. 154(b) by 135 days.

(21) Appl. No.: 16/947,653

(22) Filed: Aug. 11, 2020

(65) Prior Publication Data
US 2021/0052183 A1 Feb. 25, 2021

Related U.S. Application Data

(63) Continuation of application No. 15/550,209, filed as application No. PCT/US2016/017607 on Feb. 11, 2016, now Pat. No. 10,772,529.
(Continued)

(51) Int. Cl.
*A61B 5/00* (2006.01)
*A61B 5/024* (2006.01)
(Continued)

(52) U.S. Cl.
CPC ............ *A61B 5/374* (2021.01); *A61B 5/0006* (2013.01); *A61B 5/024* (2013.01); *A61B 5/375* (2021.01);
(Continued)

(58) Field of Classification Search
None
See application file for complete search history.

(56) References Cited

U.S. PATENT DOCUMENTS

| | | |
|---|---|---|
| 7,163,512 B1 | 1/2007 | Childre et al. |
| 8,932,218 B1 | 1/2015 | Thompson |
| (Continued) | | |

FOREIGN PATENT DOCUMENTS

| | | |
|---|---|---|
| WO | WO 2013/059833 A1 | 4/2013 |
| WO | WO 2014/006596 A1 | 1/2014 |

OTHER PUBLICATIONS

International Search Report from the U.S. Patent & Trademark Office for International Application No. PCT/US2016/017607, dated Jun. 24, 2016.
(Continued)

*Primary Examiner* — Brian T Gedeon
(74) *Attorney, Agent, or Firm* — Finnegan, Henderson, Farabow, Garrett & Dunner, LLP

(57) ABSTRACT

Systems, methods and computer-readable media are disclosed for providing therapeutic auditory stimulation. Consistent with disclosed embodiments, a system for providing therapeutic auditory stimulation may comprise a diagnostic unit that computes an EEG spectral density of a patient and a heart rate spectral density of a patient and provides values for one or more EEG frequency bands and one or more heart rate frequency bands. The system may also comprise a therapy unit that generates, based on the provided values, one or more stimulation waveforms corresponding to one or more of the EEG frequency bands and provides the stimulation waveforms for therapeutic auditory stimulation. The stimulation waveforms may comprise audible carrier frequencies modulated by signals with frequencies that vary exponentially with time. The EEG frequency bands may comprise the delta, theta, alpha, beta 1, beta 2, and gamma EEG frequency hands.

20 Claims, 11 Drawing Sheets

Related U.S. Application Data

(60) Provisional application No. 62/115,095, filed on Feb. 11, 2015.

(51) Int. Cl.
*A61N 1/36* (2006.01)
*A61N 5/06* (2006.01)
*A61B 5/374* (2021.01)
*A61M 21/00* (2006.01)
*A61B 5/375* (2021.01)
*A61N 1/372* (2006.01)
*A61B 18/00* (2006.01)
*A61N 1/05* (2006.01)

(52) U.S. Cl.
CPC ......... *A61M 21/00* (2013.01); *A61N 1/36031* (2017.08); *A61N 1/36046* (2013.01); *A61N 1/36096* (2013.01); *A61N 1/37211* (2013.01); *A61N 5/0622* (2013.01); *A61B 2018/00839* (2013.01); *A61M 2021/0027* (2013.01); *A61N 1/0551* (2013.01); *A61N 1/36085* (2013.01); *A61N 2005/065* (2013.01); *A61N 2005/0648* (2013.01)

(56) References Cited

U.S. PATENT DOCUMENTS

| | | |
|---|---|---|
| 2010/0312304 A1 | 12/2010 | York et al. |
| 2011/0105938 A1 | 5/2011 | Hardt |
| 2012/0150545 A1 | 6/2012 | Simon |
| 2013/0090519 A1 | 4/2013 | Tass |
| 2013/0184780 A1 | 7/2013 | Pless et al. |
| 2013/0267759 A1 | 10/2013 | Jin |
| 2014/0350706 A1 | 11/2014 | Morishima |

OTHER PUBLICATIONS

Written Opinion of the International Searching Authority from the U.S. Patent & Trademark Office for International Application No. PCT/US2016/017607, dated Jun. 24, 2016.

Extended European Search Report from EP Application No. 16749907. 8, dated Aug. 29, 2018.

Examination Report from EP Application No. 16749907.8, dated Apr. 24, 2019.

Summons to Attend Oral Proceedings in EP Application No. 16749907. 8, dated Oct. 7, 2019.

METHODS AND SYSTEMS FOR THERAPEUTIC NEUROMODULATION

CROSS-REFERENCE TO RELATED APPLICATIONS

This application is a continuation of U.S. patent application Ser. No. 15/550,209, which has a 371(c) date of Mar. 16, 2018, which is the National Stage of International Application No. PCT/US2016/017607, filed Feb. 11, 2016, which claims the benefit of priority to U.S. Provisional Patent Application No. 62/115,095, filed Feb. 11, 2015. Each patent application identified above is incorporated here by reference in its entirety to provide continuity of disclosure.

TECHNICAL FIELD

The disclosed embodiments generally relate to systems, methods, and computer-readable media for treating physiological and psychological disorders using auditory neuromodulation.

BACKGROUND

Stress can evoke a hypothalamic response, causing the release of hormones that in turn activate the hypothalamic-pituitary-adrenal (HPA) axis, which is involved in regulating emotions, metabolism, cognition, and the immune system. This in turn evokes a stress response which may disrupt blood sugar levels, suppress immune and inflammatory responses, interfere in memory formation, and disrupt feedback mechanisms intended to inhibit further stress responses. Chronic stress may result in impaired mental and physical health.

Existing medical treatments may have negative systemic side effects, while surgical treatments may be destructive and invasive. However, sound may be used to encode neural signals for therapeutic effect. Such auditory neuromodulation has been used to treat disorders in humans. For example, multiple studies have demonstrated that auditory neuromodulation may significantly decrease tinnitus. Tass, P. A., Adamchic, I., Freund, H. J., von Stackelberg, T., Hauptmann, C. (2012), "Counteracting tinnitus by acoustic coordinated reset neuromodulation." Adamchic, I., Hauptmann, C., Tass, P. A. (2012), "Changes of oscillatory activity in pitch processing network and related tinnitus relief induced by acoustic CR neuromodulation." Silchenko, A. N., Adamchic, I., Hauptmann, C., Tass. P. A. (2013), "Impact of acoustic coordinated reset neuromodulation on effective connectivity in a neural network of phantom sound." This subjective decrease in tinnitus may be accompanied by modification of abnormal EEG rhythms. Adamchic, I., Toth, T., Hauptmann, C., Tass, P. A. (2013). "Reversing pathologically increased EEG power by acoustic coordinated reset neuromodulation." In a rat model of antidepressant-like activity, treatment with auditory neuromodulation demonstrated effects similar to traditional chemical anti-depressants. Izvarina N. L., Lensman M. V., Murovets V. O., Savoxin A. A, "Antidepressant activity of Acoustical Neuro-Modulation in comparison with well-known antidepressants in forced swim test in rats" International Journal of Psychophysiology 69:3, September 2008, p. 288; Isvarina N. L., Lensman M. V., Murovets V. O., Savoxin A. A., "Investigation of antidepressants activity of sound beats created with different algorithms of modulation in comparison with antidepressants in forced swim test (FST) on rats." Poster, 8th IBRO World Congress of Neuroscience/Florence-Italy Jul. 14-18, 2011. A493.

Standard methods of auditory neuromodulation may only achieve temporary results, as the patient may quickly accommodate to the auditory stimulation. Consequently, there exists a need for systems and methods for providing long-term treatment of physiological and psychological disorders using auditory neuromodulation. The envisioned embodiments satisfy this need by providing therapeutic nonlinear, multi-parametric modulation of sound. This therapeutic auditory stimulation may selectively influence the activation of the HPA axis, modulating the release of neurotransmitters to influence psychological and physiological behavior. Thus this therapeutic auditory stimulation may be used to treat anxiety disorders, autism spectrum disorders, and other psychological and physiological disorders described herein.

SUMMARY

The disclosed embodiments include, for example, systems and methods for providing therapeutic auditory stimulation. This therapeutic auditory stimulation may complement or provide an alternative to medication, behavioral therapy, or other medical interventions for treatment of abnormal physiological states, including autism spectrum disorders; anxiety; post-traumatic stress disorders; depressive disorders, including depression presenting in patients with a history of post-traumatic pain; phantom pain disorders; multi-infarct dementia (Alzheimer-type vascular dementia); memory loss; mental confusion; Parkinson's disease; multiple personality disorders; headache and migraine; high blood pressure; and constipation. Additionally, and without limitation, abnormal physiological states may include type 2 diabetes, and treatment with therapeutic auditory stimulation may be used to reduce overall morbidity, improve quality of life, and decrease variations in blood glucose levels. Additionally, and without limitation, abnormal physiological states may include infant cerebral palsy, stuttering, psychosomatic disorders, and coma. In some embodiments, therapeutic auditory stimulation may be provided to a pregnant women as a preventive measure to decrease the likelihood of subsequent abnormal physiological states in her developing fetus. For example, therapeutic auditory stimulation may be provided to a pregnant women as a preventive measure to decrease the subsequent likelihood of autism spectrum disorders; anxiety; post-traumatic stress disorders; depressive disorders; and similar disorders in her developing fetus.

The disclosed embodiments may include, for example, a device for providing therapeutic auditory stimulation. The device may include a processor and a non-transitory memory. The memory may contain instructions that when executed by the processor cause the device to generate one or more stimulation waveforms. These stimulation waveforms may correspond to electroencephalographic (EEG) frequency bands. They may comprise an audible carrier frequency modulated by signals with frequencies that vary non-linearly with time. The device may also include means for providing one or more of the stimulation waveforms to a patient as therapeutic auditory stimulation. For example, the device may include local means for providing the signal, including electronic devices such as music players, computers, or smartphones. As an additional example, local means for providing the signal may include medical products, such as special purpose therapeutic devices. The providing means may also include remote means for providing the signal. Remote provide means may comprise means for storing and transmitting the stimulation signal so that the generation of stimulation signal may be temporally or spatially separated from the provision of the stimulation signal. Storage means may include non-transitory computer-readable media, such as magnetic tape or magnetic disks, optical disks, flash memory, or read-only memory. Transmission means may include computer networks, telephone networks, or the physical transmission of the above storage media.

In certain embodiments, EEG frequency bands may include a low-frequency band and a high-frequency band. The stimulation waveform corresponding to the low-frequency band may be provided before the stimulation frequency corresponding to the high frequency band. In certain embodiments, the stimulation waveform corresponding to the high-frequency band may be provided before the stimulation frequency corresponding to the low frequency band.

In certain embodiments, the stimulation waveforms may comprise pairs of frequency intervals, the pairs including increasing frequency intervals and decreasing frequency intervals, the modulating signal frequencies increasing exponentially during the increasing frequency intervals and decreasing exponentially during the decreasing frequency intervals. In some embodiments, the durations of the pairs may vary non-linearly. In some embodiments, the durations of the decreasing frequency intervals may exceed durations of the increasing frequency intervals. In some embodiments, the durations of the frequency intervals may be approximately related by a constant multiple. This constant multiple may be the golden ratio.

In certain embodiments, the EEG frequency bands may be selected from the group consisting of the delta, theta, alpha, beta 1, beta 2, and gamma EEG frequency bands.

The disclosed embodiments may also include, for example, a system for providing therapeutic auditory stimulation. This system may include a diagnostic unit configured to compute an EEG spectral density and a heart rate spectral density of a patient. The unit may provide values for one or more EEG frequency bands and one or more heart rate frequency bands. The system may include a therapy unit that generates, based on the values provided by the diagnostic unit, one or more stimulation waveforms corresponding to one or more of the EEG frequency bands. The therapy unit may provide the stimulation waveforms for therapeutic auditory stimulation.

In certain embodiments, the diagnostic unit may include an electroencephalograph comprising two or more occipital electrodes. In certain embodiments the diagnostic unit may calculate the sympathovagal balance of the patient. In some embodiments, the stimulation waveforms may comprise audible carrier frequencies modulated by signals with frequencies that vary exponentially with time. In various embodiments, the modulating signal frequencies may increase exponentially from the beginning to the end of each stimulation waveform. In some embodiments, the stimulation waveforms may comprise pairs of frequency intervals. The pairs may include increasing frequency intervals and decreasing frequency intervals. The modulating signal frequencies may increase exponentially during the increasing frequency intervals and decreasing exponentially during the decreasing frequency intervals. The durations of the pairs may vary non-linearly. The durations of the decreasing frequency intervals may exceed durations of the increasing frequency intervals. The durations of frequency intervals may be approximately related by a constant multiple. The constant multiple may be the golden ratio.

In some embodiments, the EEG frequency bands may comprise the delta, theta, alpha, beta 1, beta 2, and gamma EEG frequency bands. In some embodiments, the stimulation waveforms may be generated remotely from the therapeutic auditory stimulation. In certain embodiments, the first stimulation waveform may be provided for therapeutic auditory stimulation telephonically.

The disclosed embodiments may include, for example, a method for providing therapeutic auditory stimulation. The method may comprise receiving an indication of an abnormal physiological state of a patient. The method may comprise generating a first stimulation waveform based on the indication. The first stimulation waveform may correspond to a first EEG frequency band. The first stimulation waveform may comprise an audible carrier frequency modulated by a first signal with an exponentially varying frequency. The method may comprise providing the first stimulation waveform for first therapeutic auditory stimulation.

In certain embodiments, a maximum frequency of the first signal may correspond to a maximum frequency associated with the first EEG frequency band. In some embodiments, the method may further comprise generating a second stimulation waveform based on the indication. The second waveform may correspond to a second EEG frequency band and may comprise an audible carrier frequency modulated by a second signal with an exponentially varying frequency. The method may further comprise providing the second stimulation waveform for second therapeutic auditory stimulation.

In certain embodiments, the duration of the increasing frequency interval and the decreasing frequency interval may depend on the first EEG frequency band. In some embodiments, the indication may be based on electroencephalography and sympathetic-vagal balance measurement of the patient. In various embodiments, the first stimulation waveform may be provided for first therapeutic auditory stimulation on a computer-readable medium.

The disclosed embodiments may include, for example, a method for providing therapeutic auditory stimulation. The method may include measuring, using a portable electroencephalograph, the sympathovagal balance of a patient and the contributions from one or more EEG frequency bands to an EEG of the patient. The method may also include generating a train of stimulation waveforms. The train of stimulation waveforms may be based on an indication of an abnormal physiological state of a patient. One of the stimulation waveforms may correspond to an EEG frequency band and may comprise an audible carrier frequency modulated by a signal. The signal may include frequency intervals comprising increasing frequency intervals during which the frequency of the signal increases exponentially. The frequency intervals may comprise decreasing frequency intervals during which the frequency of the signal decreases exponentially. The durations of the increasing frequency intervals and the decreasing frequency intervals may vary and may depend on the EEG frequency band corresponding to the stimulation waveform. The method may comprise providing the stimulation waveforms to an audio speaker for generating therapeutic auditory stimulation for the patient.

In certain embodiments, the train of stimulation waveforms may be generated remotely from the audio speaker. In various embodiments, the method may further comprise storing the train of stimulation waveforms in a non-transitory memory before providing the stimulation waveforms to the audio speaker. In some embodiments, a telephone may comprise the audio speaker.

The disclosed embodiments may include, for example, a computer-readable medium comprising instructions that cause a computer to perform the operations for providing therapeutic auditory stimulation. The operations may comprise generating a train of stimulation waveforms based on an indication of an abnormal physiological state of a patient. One of the stimulation waveforms may correspond to an EEG frequency band and may comprise an audible carrier frequency modulated by a signal. The signal may include frequency intervals comprising increasing frequency intervals during which the frequency of the signal increases exponentially and decreasing frequency intervals during which the frequency of the signal decreases exponentially. The duration of the frequency intervals may be related by an approximately constant multiple.

It is to be understood that both the foregoing general description and the following detailed description are exemplary and explanatory only and are not restrictive of the disclosed embodiments, as claimed.

BRIEF DESCRIPTION OF THE DRAWINGS

The drawings are not necessarily to scale or exhaustive. Instead, emphasis is generally placed upon illustrating the principles of the inventions described herein. The accompanying drawings, which are incorporated in and constitute a part of this specification, illustrate several embodiments consistent with the disclosure and together with the description, serve to explain the principles of the disclosure. In the drawings.

DETAILED DESCRIPTION

Consistent with disclosed embodiments, the envisioned therapeutic auditory stimulation may be used to treat autism spectrum disorders; anxiety; post-traumatic stress disorders; depressive disorders, including depression presenting in patients with a history of post-traumatic pain; phantom pains disorders; multi-infarct dementia (Alzheimer-type vascular dementia); memory loss; mental confusion; Parkinson's disease; multiple personality disorders; headache and migraine; high blood pressure; and constipation. In patients with type 2 diabetes, therapeutic auditory stimulation may be used to reduce overall morbidity, improve quality of life, and decrease variations in blood glucose levels. Therapeutic stimulation may be used to treat infant cerebral palsy, stuttering, psychosomatic disorders, and coma. In some embodiments, therapeutic auditory stimulation may be provided to a pregnant women as a preventive measure to decrease the likelihood of subsequent abnormal physiological states in her developing fetus. For example, therapeutic auditory stimulation may be provided to a pregnant women as a preventive measure to decrease the subsequent likelihood of Autism spectrum disorders; anxiety; post-traumatic stress disorders; depressive disorders; and similar disorders in her developing fetus.

Figure 1:
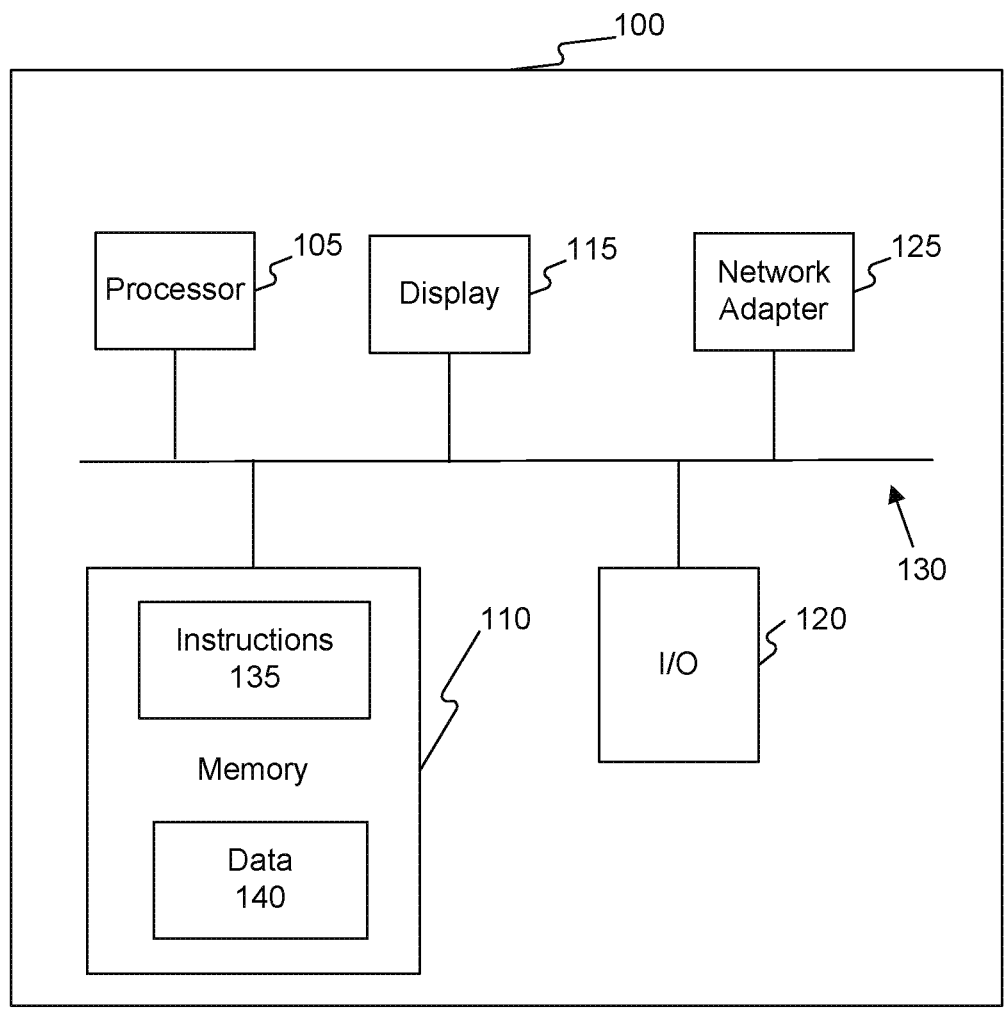
FIG. 1 depicts an exemplary electronic device for providing therapeutic stimulation.

FIG. 1 depicts an exemplary electronic device for providing therapeutic stimulation, consistent with disclosed embodiments. This electronic device may comprise exemplary computing system 100. In some embodiments, system 100 may include a processor 105 and a non-transitory memory 110. In certain embodiments, system 100 may (but need not) include one or more of a display 115, I/O interface(s) 120, and network adapter 125. These units may communicate with each other via bus 130 and/or wirelessly, or a combination thereof. In various embodiments, processor 105 may be one or more microprocessors or central processor units (CPUs) performing processing operations. Memory 110 may be a volatile or non-volatile, magnetic, semiconductor, tape, optical, removable, non-removable, or other type of storage device or tangible (i.e., non-transitory) computer-readable medium. In various embodiments, memory 110 may store data 140 reflecting any type of information in any format that the system may use to perform operations consistent with the disclosed embodiments. Memory 110 may store instructions 135 to enable processor 105 to execute one or more applications, including program(s). Alternatively, the instructions, application programs, etc., may be stored in an external storage in communication with server(s) via a network. Display 115 may be any device which provides a visual output, for example, a computer monitor, an LCD screen, etc. I/O interface 120 may include, for example, a keyboard, a mouse, an audio input device, a touch screen, or an infrared input interface. Network adapter 125 may enable device 100 to exchange information with external networks. In various embodiments, network adapter 125 may include a wireless wide area network (WWAN) adapter, or a local area network (LAN) adapter. Consistent with disclosed embodiments, the components shown in FIG. 1 may reside in a single device or multiple devices.

Figure 2A:
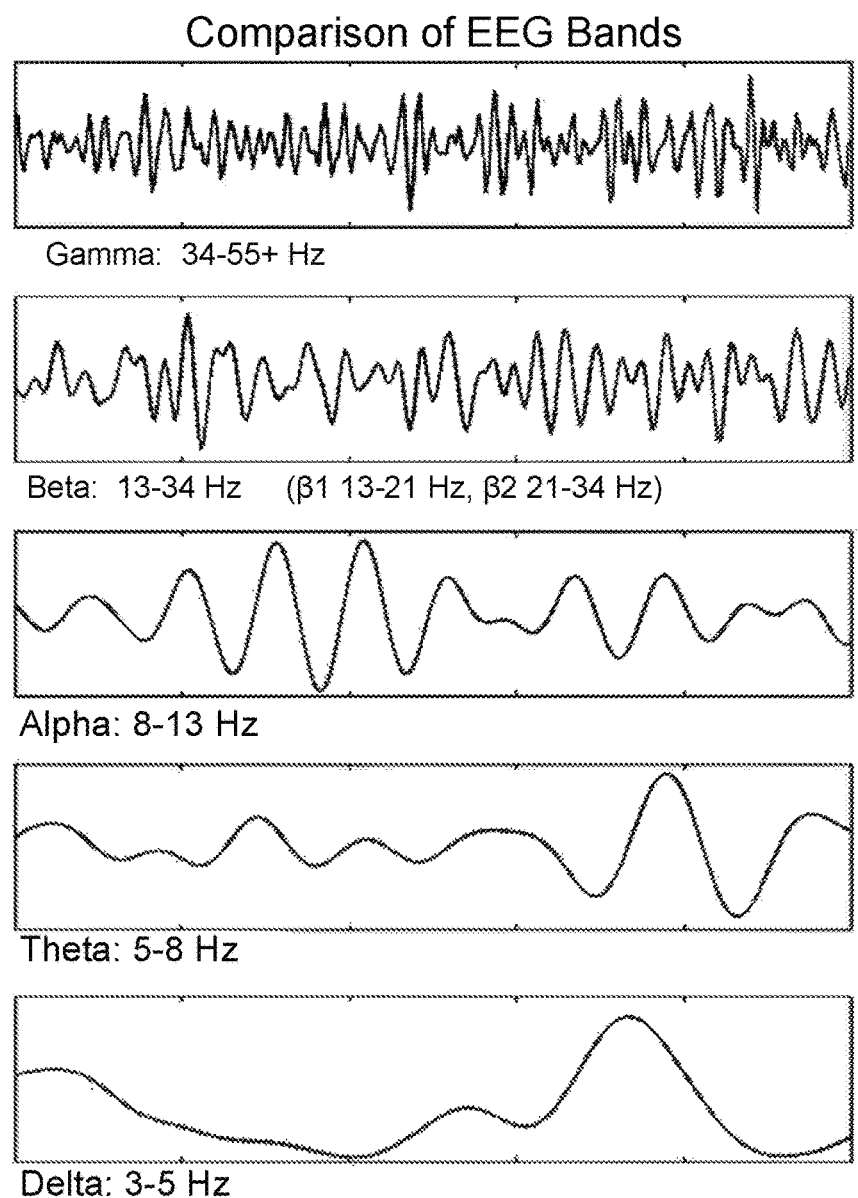
FIG. 2A depicts an exemplary classification of the EEG power spectrum into frequency bands.

FIG. 2A depicts an exemplary classification of the EEG power spectrum into frequency bands. An electroencephalogram is a recording of the electrical activity of a patient's brain. Both the time domain and the frequency domain representation of the EEG signal may be of diagnostic value. The power spectrum of the EEG signal may be divided into distinct bands. These bands may be even spaced on a logarithmic scale, meaning that the frequencies defining a band are approximately fixed multiples of the frequencies defining the preceding band. As an illustrative example, the upper frequency for alpha waves (13 Hz) may be approximately 1.7 times the upper frequency for theta waves (8 Hz), which in turn may be approximately 1.75 times the upper frequency for the delta wave band (5 Hz). The fixed multiple may approximate the golden ratio ($\phi$), an irrational number.

Functionally, this relationship reduces entrainment and cross-talk between signals in the different frequency bands.

One of ordinary skill in the art would recognize that other categorizations of EEG power spectral density, differing in number or arrangement of bands, are possible. The categorization illustrated in FIG. 2A includes alpha, beta 1, beta 2, gamma, delta, and theta bands. Though this categorization includes minimum and maximum frequencies, those frequencies do not define the bands. Instead, the bands correspond to mental states or processes and are defined with reference to those processes. As used herein, when two bands are considered, the high-frequency band may have a higher maximum frequency, and the low-frequency band may have a lower minimum frequency. In certain aspects, the high-frequency band and the low frequency band may be distinct. For example, when an alpha band and a beta band are considered, the beta band is the high-frequency band and the alpha band is the low-frequency band. When a beta band and a theta band are considered, the beta band is the high-frequency band and the theta band is the low-frequency band.

Gamma waves are patterns of neural oscillation corresponding to higher mental activity, such as perception, problem solving and emotions, and consciousness. In some embodiments, gamma waves may be defined as encompassing waves with frequencies ranging from 25-100+ Hz. More preferably, gamma waves may be defined as encompassing waves with frequencies ranging from 34-55 Hz.

Beta waves are patterns of neural oscillation corresponding to active, busy, or conscious thinking. Beta waves may correspond to active concentration, arousal, and cognition. In some embodiments, beta waves may be defined as encompassing waves with frequencies ranging from 13-34 Hz. More preferably, Beta 1 waves may be defined as encompassing waves with frequencies ranging from 13-21 Hz and Beta 2 waves may be defined as encompassing waves with frequencies ranging from 22-34 Hz.

Alpha waves are patterns of neural oscillation corresponding to awake relaxation and pre-awake or pre-sleep drowsiness. In some embodiments, alpha waves may be defined as encompassing waves with frequencies ranging from 8-13 Hz.

Theta waves are patterns of neural oscillation corresponding to deep meditative, drowsy, or dreaming states. Strong or persistent theta waves may indicate brain pathologies. In some embodiments, theta waves may be defined as encompassing waves with frequencies ranging from 5-8 Hz.

Delta waves are patterns of neural oscillation corresponding to dreamless sleep with loss of body awareness. In some embodiments, theta waves may be defined as encompassing waves with frequencies ranging from 3-5 Hz.

Consistent with disclosed embodiments, abnormal mental states may be identified using EEGs. For example, anxiety or depression may be indicated by increased power in the alpha and beta EEG bands. As an additional example, patients with attention deficit disorder may present with increased power in theta EEG bands and an increase in the beta EEG band as compared to the gamma EEG band. As described below, altering the power in EEG bands may have therapeutic effect. For example, increasing and decreasing the contribution of the alpha EEG band may provide a treatment for anxiety.

Figure 2B:
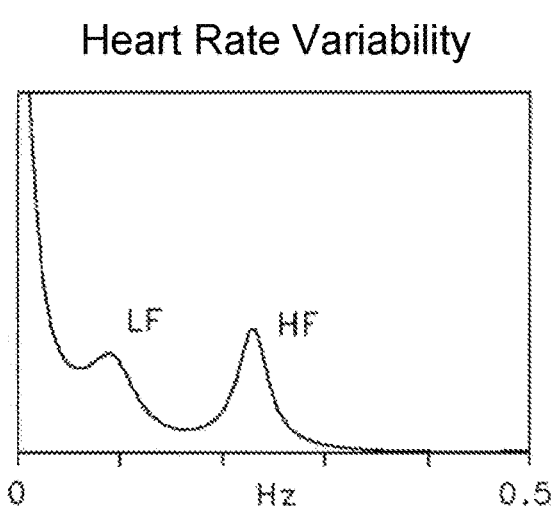
FIG. 2B depicts an exemplary transformation of a heart rate signal into the frequency domain.

FIG. 2B depicts an exemplary transformation of a heart rate signal into the frequency domain, consistent with disclosed embodiments. In some embodiments this transformation may be a heart rate power spectral density. In certain aspects, the interval between heartbeats may reflect nervous system activity, such as autonomic nervous system activity, affecting the heart rate. For example, this interval may depend on the balance between sympathetic and vagal activation of the heart (i.e. the sympathovagal balance). Abnormal sympathetic or vagal activation may indicate an abnormal physiological state, such as an abnormal mental state. As a non-limiting example, abnormal activation may indicate anxiety, depression, panic disorders, post-traumatic stress disorders, autism spectrum disorders, or other disordered mental states as known by one of skill in the art. Time domain statistics, such as the standard deviation of the heart rate interval or the mean-squared difference between successive heart rate intervals may indicate abnormal nervous system activity. Frequency domain statistics, such as contributions to the power spectral density of the heart rate interval, may also indicate abnormal nervous system activity. For example, FIG. 2B depicts the low and high frequency components of the power spectral density of heartbeat interval times. As described below, the magnitude of the components may be computed using various techniques known to one of skill in the art. The low frequency component of the power spectral density may be associated with fluctuations in sympathetic nerve activity. The high frequency component may be associated with fluctuations of vagal-cardiac nerve activity. The ratio of the low frequency component to the high frequency component may indicate the relative contributions of sympathetic and parasympathetic autonomic nervous system components to the heart rate. Abnormalities in this balance may indicate abnormal mental states and can be used as diagnostic criteria in selecting appropriate therapeutic auditory stimulation.

Consistent with disclosed embodiments, therapeutic auditory stimulation may provide auditory signals comprising certain waveforms corresponding to different EEG bands. As discussed below with respect to FIGS. 7A-7D, the stimulation waveforms may vary non-linearly in duration, frequency, and rate of change of frequency. The correspondence between a stimulation waveform and an EEG band may be functional. For example, providing the stimulation frequency may affect the contribution of that EEG band to the overall power spectrum of the EEG. In some aspects, the contribution may be reduced. This functional relationship may be based on a correspondence between frequency parameters of the stimulation waveform and the frequency parameters of the corresponding EEG bands.

As described, in response to the therapeutic auditory stimulation, the contribution from corresponding EEG bands may change. This change may at least temporarily persist once the external stimulation is removed. Consistent with disclosed embodiments, therapeutic mental or behavioral changes may arise from this change. In some embodiments, some common mechanism may generate both the observed change in EEG contributions and the therapeutic mental or behavioral changes. For example, providing therapeutic stimulation corresponding to the alpha EEG band described above may cause a decrease in the contribution of the alpha EEG band. This decrease may cause, or be associated with, an increase in alertness and a reduction in symptoms of depression.

Envisioned systems and methods may use a perceptible carrier signal to provide otherwise imperceptible signals, consistent with disclosed embodiments. In some embodiments, the perceptible carrier signal may be an audible carrier signal. In certain aspects, this audible carrier signal may include audible carrier frequency waveforms. For example, the auditory frequency range may be considered to extend approximately from 20 Hz to 20 kHz. Therapeutic auditory stimulation corresponding to alpha, theta, delta, or similar brain waves may be provided using a carrier wave at an audible carrier frequency modulated by a modulating signal corresponding to the targeted EEG band. While therapeutic auditory stimulation is disclosed in this application, one of skill in the art would recognize that the same disclosed stimulation signals could be used to provide other forms of therapeutic stimulation suitable for other sensory organs. For example, the disclosed stimulation signals could be provided to the eyes of the patient using light as visual therapeutic stimulation, or to the skin using pressure, heat, or electrical stimulation as tactile therapeutic stimulation. While amplitude modulation of the perceptible carrier signal is disclosed in this embodiment, the form of modulation depends only on the targeted sensory organ and may include any one or more of amplitude, frequency, phase, or other signal characteristics known to one of skill in the art.

Envisioned systems and methods may use stimulation signals with multiple non-linear aspects, consistent with disclosed embodiments. These non-linear aspects may include non-linear changes in modulating signal frequency, amplitude, phase, or other signal characteristics known to one of skill in the art. These changes may occur at rates and over time durations that also vary in a non-linear manner. In some embodiments, these non-linear aspects of the stimulation signals may enhance the effect of the therapeutic signal. For example, these non-linear aspects of the signal may prevent accommodation by the nervous system of the patient to the therapeutic stimulation.

Figure 3:
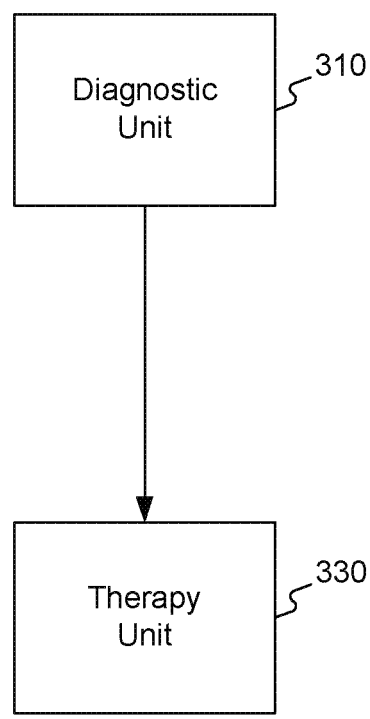
FIG. 3 depicts a block diagram illustrating an exemplary system for providing therapeutic auditory stimulation.

FIG. 3 depicts a block diagram of an exemplary system for providing therapeutic auditory stimulation consistent with disclosed embodiments. According to some embodiments, the exemplary system may comprise a diagnostic unit 310 and a therapy unit 330. In some embodiments, a single device may comprise diagnostic unit 310 and therapy unit 330. In certain embodiments, therapy unit 330 may comprise one or more devices distinct from diagnostic device 310. For example, diagnostic unit 310 may comprise a potable EEG device and therapy unit 330 may comprise a computing device controlling an audio output. For example therapy unit 330 may comprise a music player, mobile device, tablet computer, laptop computer, special purpose PC card (e.g. PC, PCMCIA, ExpressCard, or similar modules), desktop computer, or server. The audio output may comprise one or more speakers and/or headphones. In some embodiments, the computing device may be configured with special purpose instructions. In certain aspects, these special purpose instructions may configure the computing device to perform one or more of the functions of generating therapeutic auditory stimulation, analyzing EEG and/or heart rate variability signals, and managing stored therapeutic auditory stimulation waveforms. In some aspects, the stored waveforms may be stored in European Data Format (edf) files. In some embodiments, elements of the disclosed exemplary system may comprise electronic devices as described with reference to FIG. 1.

Diagnostic unit 310 may receive indications of the condition of a patient, consistent with disclosed embodiments. In certain embodiments, diagnostic unit 310 may process these indications, transforming them to enable diagnosis of a condition. In certain embodiments, a user may determine appropriate therapeutic auditory stimulation based on the processed indications. In various embodiments, the diagnostic unit may automatically determine, using a processor, appropriate therapeutic auditory stimulation based on the processed indications. For example, diagnostic unit 310 may use a processor to access a lookup table stored in a memory to determine appropriate therapeutic auditory stimulation. As an additional example, diagnostic unit 310 may use a processor to implement a decision tree or a learning algorithm, such as a machine learning algorithm, to determine appropriate therapeutic auditory stimulation. Other methods of automatically determining therapeutic stimulation based on processed patient data may also be used, as would be known by one of skill in the art.

Diagnostic unit 310 may comprise a signal conditioning unit and a signal processing unit, consistent with disclosed embodiments, as described below with reference to FIG. 4. These units may comprise one or more electronics devices. For example, consistent with disclosed embodiments, a special-purpose computer, such as an EEG machine, may comprise one or more of the signal conditioning and signal processing units. In some embodiments, the EEG machine may portable. For example, the EEG machine may be less than or comparable to a laptop computer in dimension and weight. In certain embodiments a general-purpose computer such as a workstation, desktop, laptop, smartphone, tablet computer or similar computing device comprise one or more of the signal conditioning and signal processing units, in combination with one or more additional data-acquisition components.

Therapy unit 330 may be configured based on indications received by diagnostic unit 310. In some embodiments, diagnostic unit 310 may automatically provide therapy unit 330 an indication of the appropriate therapeutic auditory stimulation. As an additional example, diagnostic unit 310 may provide values that therapy unit 330 uses to generate therapeutic auditory stimulation. In other embodiments, a user may configure therapy unit 330 based on indications provided by diagnostic unit 310. As described below with reference to FIG. 5, therapy unit 330 may comprise means for generating the stimulation signal. Additionally or alternatively, therapy unit 330 may comprise means for providing therapeutic auditory stimulation to one or more patients.

Therapy unit 330 may comprise one or more devices communicatively connected to diagnostic unit 310, consistent with disclosed embodiments. For example, diagnostic unit 310 may transmit and/or receive information over a computer network connection or a telephonic connection with therapy unit 330. A computer network connection may include one or more wireless links. A telephonic connection may include one or more cellular links. Additionally or alternatively, a user may configure therapy unit 330 using data or indications provided by diagnostic unit 310.

Figure 4A:
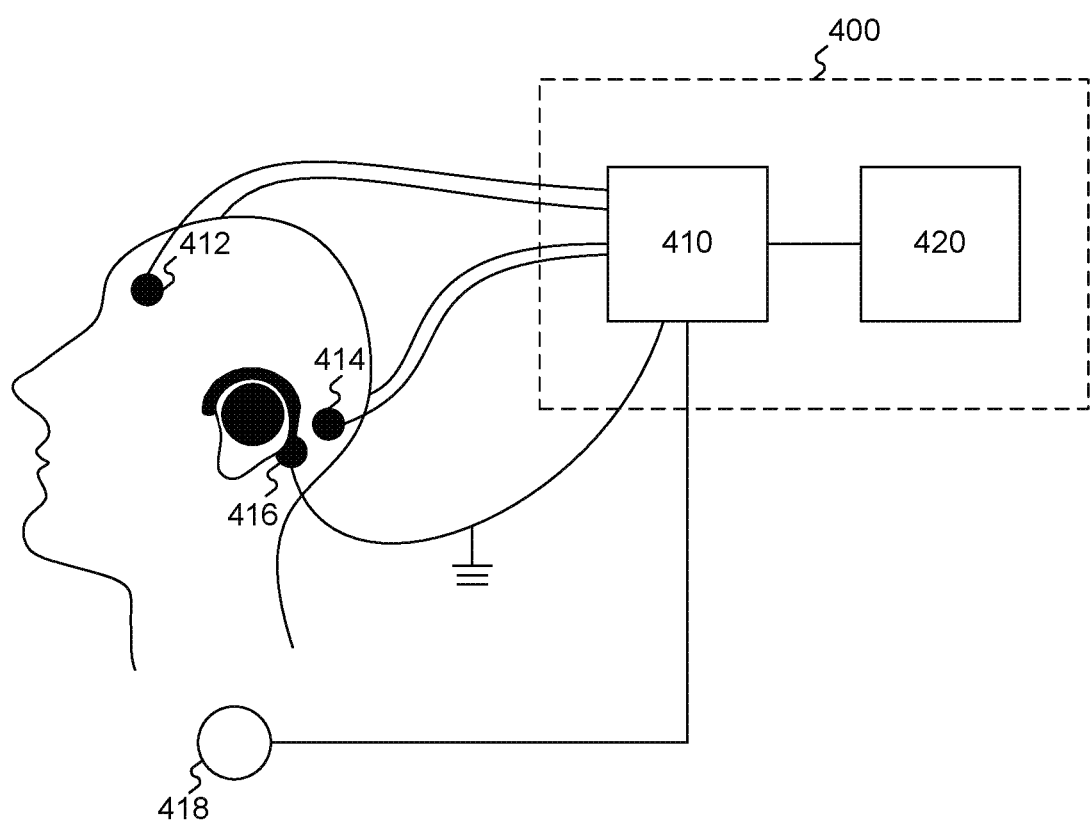
FIG. 4A depicts a block diagram illustrating an exemplary diagnostic unit for receiving indications of the condition of a patient.

FIG. 4 depicts a block diagram illustrating an exemplary diagnostic unit for receiving indications of the condition of a patient, consistent with disclosed embodiments. In some embodiments, diagnostic unit 310 may comprise one or more electronics devices. For example, diagnostic unit 310 may comprise a signal conditioning and registration device 400, electrodes (such as electrodes 412 and 414), and heart rate monitor 418. In some embodiments, signal conditioning and registration device 400 may be a single device, such as an EEG machine. In certain embodiments signal conditioning and registration device 400 may comprise multiple devices, such as a data acquisition unit and a general-purpose computer configured to process data received from the data acquisition unit.

Signal conditioning unit 410 may comprise electronic components consistent with disclosed embodiments. In some embodiments, signal conditioning unit 410 may comprise one or more connectors for electrodes. Signal conditioning unit may comprise one or more connectors for signal processing unit 420. In certain embodiments, signal conditioning unit 410 may comprise active components, passive components, and electromechanical components. For example, signal conditioning unit 420 may comprise amplifiers, filters, connectors, analog-to-digital connectors, digital-to-analog connectors, microcontrollers, processors, and/or memories.

Signal conditioning unit 410 may receive one or more EEG signals from one or more electrodes consistent with disclosed embodiments. In some embodiments, signal conditioning unit 410 may condition the one or more electrical signals in preparation for, or as part of data acquisition, consistent with disclosed embodiments. In some embodiments, the EEG electrical signals may correspond to measurements of electrode potential. For example, EEGs signals may correspond to differential measurements of electrode potential between multiple electrodes. In some embodiments, the one or more electrodes may include a reference electrode. A differential measurement may depend on the difference between the electrical potential of the reference electrode and the electrode potential of another electrode. In some embodiments, the reference electrode may be connected to ground. In certain embodiments, the EEG signals may correspond to single-ended or pseudo-differential measurements of electrode potentials.

Signal conditioning unit 410 may receive a heart rate signal from a heart rate monitor 418 consistent with disclosed embodiments. In some embodiments, heart rate monitor 418 may comprise one or more electrodes and may provide an ECG signal. In certain embodiments, heart rate monitor 418 may comprise a pulse oximetry unit and may provide a blood oxygenation signal.

Signal conditioning unit 410 may modify the received signals (the EGG signals and the heart rate signal) consistent with disclosed embodiments. In some embodiments, signal conditioning unit 410 may provide the received signals in a suitable format for signal processing unit 420. For example, signal conditioning unit 410 may amplify the received signals. As an additional example, signal conditioning unit 410 may digitize the received signals. Signal conditioning unit 410 may determine a heart rate series from the heart rate signal. In some embodiments, signal conditioning unit 410 may provide the received signals to signal processing unit 420 wirelessly, such as over a Wi-Fi network, using Bluetooth, or other methods of wireless data transmission known to one of skill in the art. Signal conditioning unit 410 may provide the signals over a network, such as a computer network.

Signal conditioning unit 410 may filter one or more of the received signals consistent with disclosed embodiments. For example, filter parameters may be chosen to reject high frequency noise while preserving relevant EEG signals. As an additional example, filter parameters may be chosen to reject low frequency noise while preserving relevant EEG signals. In some embodiments, the bandwidth of the filtered EEG signals provided by the signal conditioning unit 410 may be 0.1 Hz to 100 Hz. Similarly, filter parameters may be chosen to reject high frequency noise while preserving relevant heart rate signals. As an additional example, filter parameters may be chosen to reject low frequency noise while preserving relevant heart rate signals. Filtering may be accomplished in hardware or software.

Signal conditioning unit 410 may electrically isolate the patient from the signal processing unit 420 consistent with disclosed embodiments. For example, signal conditioning unit 410 may magnetically, optically, or capacitively isolate the patient from the signal processing unit 420. In some embodiments, such isolation may be for the protection of the patient. In certain embodiments, such isolation may be for the protection of the Signal Processing Unit 420.

This description of signal conditioning unit 410 is intended to illustrate a potential embodiment of the disclosed systems and methods and is not intended to be limiting. One of skill in the art would recognize that other configurations and arrangements are possible.

Signal processing unit 420 may comprise electronic components consistent with disclosed embodiments. Signal processing unit 420 may comprise a memory, a processor, and a bus. Signal processing unit 420 may comprise an input/output unit and a display. Signal processing unit 420 may be connected to a computer network. As a non-limiting example, signal processing unit 420 may be a computer connected to signal conditioning unit 410 by a universal serial bus cable.

Signal processing unit may receive conditioned signals from signal conditioning unit 410 consistent with disclosed embodiments. In some embodiments, signal processing unit 410 may receive analog signals. Signal processing unit 420 may digitize analog signals received from signal conditioning unit 410. In some embodiments, signal processing unit 420 may receive digital signals from signal conditioning unit 410. Signal processing unit 420 may transmit and/or receive data from signal conditioning unit 410 through a wired connection or a wireless connection. Signal processing unit 420 may transmit and/or receive data from signal conditioning unit 410 over a network. In some embodiments, the input/output unit may comprise one or more connectors for connecting to signal conditioning unit 410.

Signal processing unit 420 may filter signals received from signal conditioning consistent with disclosed embodiments. For example, signal processing unit 420 may filter received EEG signals using analog or digital filters. Filter parameters may be chosen to reject noise while preserving EEG signals according to well-known filter design methods readily known to one of skill in the art. In some embodiments, the bandwidth of the filtered EEG signals may be 0.1 Hz to 100 Hz. As an additional example, signal processing unit 420 may filter a heart rate signal received from the signal conditioning unit. Filtering may be accomplished in hardware or software.

Signal processing unit 420 may amplify signals received from signal conditioning unit 410 consistent with disclosed embodiments. Signal processing unit 420 may acquire analog signals consistent with disclosed embodiments. Signal processing unit 420 may amplify received signals for purposes of convenient analysis, for example by normalizing signals.

Signal processing unit 420 may transform signals received from signal conditioning unit 410 consistent with disclosed embodiments. For example, signal processing unit 420 may compute a power spectral density of one or more of the received EEG signals. Signal processing unit 420 may determine a total signal power from the power spectral density. Signal processing unit 420 may determine signal powers for EEG bands from the power spectral density. Signal processing unit 420 may determine the contribution of one or more EEG signal bands to the total power for the signal. For example, signal processing unit 420 may determine the fraction of the total signal power contributed by the components of the EEG signal in the delta wave EEG band. The relative contributions of the EEG signals may indicate a mental state of the patient. For example, excessive contributions from lower-frequency EEG bands may indicate a depressive disorder. Conversely, excessive contributions from higher-frequency EEG bands may indicate an anxiety disorder.

Signal processing unit 420 may also determine a heart rate series from the heart rate signal consistent with disclosed embodiments. Signal processing unit 420 may receive a heart rate series from the signal conditioning unit 410. Signal processing unit 420 may transform the heart rate series into a power spectral density. In some embodiments, this transformation may use parametric methods such a fast Fourier transform, non-parametric methods such as autoregressive models, or other methods known to those of skill in the art. In some embodiments, the power spectral density may comprise components at varying frequencies. For example, the power spectral density may comprise a low frequency component associated with fluctuations sympathetic nerve activity. In some embodiments this low frequency component may be centered on a frequency in the range of 0.04-0.15 Hz. As another example, in some embodiments the power spectral density may comprise a high frequency component associated with fluctuations of vagal-cardiac nerve activity. In some embodiments this high frequency component may be centered on a frequency in the range of 0.15-40 Hz. Signal processing unit 420 may determine a ratio of the low frequency components to the high frequency components of the power spectrum. This ratio may indicate the balance between the contributions of the sympathetic and parasympathetic components of the autonomic nervous system to the heart rate. For example, a reduced ratio or decreased contribution from high-frequency components may indicate a depressive or an anxiety disorder. Other measures known to one of skill in the art, such as the standard deviation the heart rate period, may also provide indications of the mental state of the patient. Thus the disclosed embodiments are not intended to be limiting.

Signal processing unit 420 may display information consistent with disclosed embodiments. For example, signal processing unit 420 may display information corresponding to one or more received signals. In some embodiments, signal processing unit 420 may display frequency domain information for a received EEG signal. For example, signal processing unit 420 may display the normalized contribution to the total EEG signal power from one or more EEG bands. In certain embodiments, signal processing unit 420 may display heart rate information. For example, signal processing unit 420 may display statistics related to heart rate variability. In some embodiments, signal processing unit 420 may display the ratio of the low frequency components of the heart rate power spectrum to the high frequency components of the heart rate power spectrum.

This description of signal processing unit 420 is intended to illustrate a potential embodiment of the disclosed systems and methods and is not intended to be limiting. One of skill in the art would recognize that other configurations and arrangements are possible.

The signal conditioning unit 410 may be connected to electrodes for recording electrical activity on the scalp. This electrical activity may result from the activity of the brain of a patient. Many configurations of electrodes, differing in number and placement, are suitable for use with the disclosed systems and methods. Standardized electrode placements include the 10-20 system, which includes 21 electrodes, and the extended 10-20 system, or 10% system, which includes 74 electrodes. Consistent with the disclosed systems and embodiments, electrodes may be placed at some or all of the locations described in these standards. For example, consistent with disclosed embodiments, frontal electrodes 412 may be placed bilaterally over the frontal lobes of the patient and occipital electrodes 414 may be placed bilaterally over the occipital lobes of the patient. In some embodiments, a reference electrode may be placed on, behind, or near an ear of the patient. In certain embodiments, this reference electrode may be connected to ground. As would be recognized by one of skill in the art, alternative electrode placement locations may be used. The described electrode position is not intended to be limiting.

Electrodes, such as occipital electrodes 414, may be disc electrodes, cup electrode, needle electrodes, or other suitable electrode types known to one of skill in the art. In some embodiments electrodes may be attached to the patient. For example, electrodes may be attached using collodion or other adhesives. In certain embodiments, headbands, straps, or caps may hold one or more electrodes in place. In certain embodiments, conductive jelly or conductive paste may be placed between the electrodes and the patient to reduce the impedance of the electrode-patient interface. In certain embodiments, dry electrodes or capacitive electrodes may be used. Active electrodes or passive electrodes may be used, consistent with disclosed embodiments.

This description of diagnostic unit 400 is intended to illustrate potential embodiments of the disclosed systems and methods. This description is not intended to limit the disclosed systems and methods to any particular device or arrangement of devices. One of skill in the art would recognize other possible configurations and arrangements consistent with disclosed embodiments. For example, electrodes, signal conditioning unit 410 and signal processing unit 420 may each comprise multiple devices that together perform the disclosed functions. Conversely, a single device may perform the functions of the electrodes, signal conditioning unit 410, and signal processing unit 420.

The envisioned systems and methods may use quantitative EEG for diagnosis and patient monitoring. For example, quantitative EEG may be used to generate neuroimages showing regions of abnormal neural activity in the brain of a patient. This quantitative EEG may be obtained using devices and methods known to one of skill in the art. In certain aspects, diagnostic unit 310 may comprise a quantitative EEG system.

In some embodiments, the envisioned systems and methods may use low-resolution brain electromagnetic tomography (LORETA) for diagnosis and patient monitoring. As would be recognized by one of skill in the art, LORETA may be used to diagnose abnormal mental states, such as depression, anxiety disorders, and ADHD. In certain aspects, diagnostic unit 310 may comprise a LORETA system.

Figure 4B:
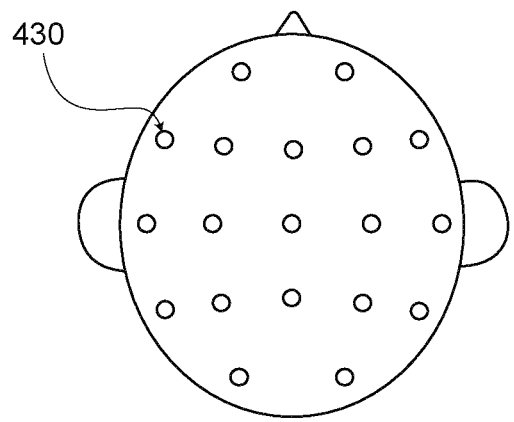
FIG. 4B depicts an exemplary schematic of an electrode placement arrangement for quantitative or LORETA EEG.
Figure 4C:
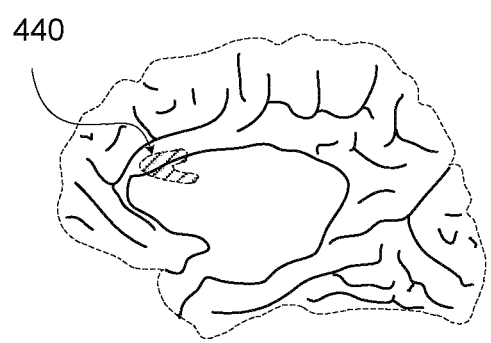
FIG. 4C depicts an exemplary illustration of the use of quantitative or LORETA EEG to localize a region of abnormal neural activity for diagnostic and monitoring purposes.

Consistent with disclosed embodiments, a quantitative EEG system or LORETA system may be configured to record multichannel EEG data. In certain aspects, the system may use electrodes, such as electrode 430, for recording the EEG data. In some aspects, as shown in FIG. 4B, such electrodes may contact the head of the patient in a particular pattern. For example, nineteen channels of EEG data may be collected from nineteen electrodes arranged on the head of the patient, each measured with respect to a reference electrode. As shown in FIG. 4C, quantitative EEG systems, LORETA systems, and similar systems known to one of skill in the art may use such multichannel EEG recordings to determine neural activity levels. For example, such systems may be configured to identify regions, such as region 440, in which neural activity levels are abnormally high or abnormally low. In some aspects, this identification may rely on the determined neural activity levels. In certain aspects, this identification may rely on a comparison between the determined neural activity levels and historical data. This historical data may be specific to a patient, or may reflect historical data for a population of patients. In some embodiments, the historical data and the determined neural activity levels may be used to calculate a statistic, such as a Z statistic or similar statistical measure, for identifying regions of abnormal neural activity. As would be recognized by one of skill in the art, the preceding description is not intended to be limiting.

Figure 5:
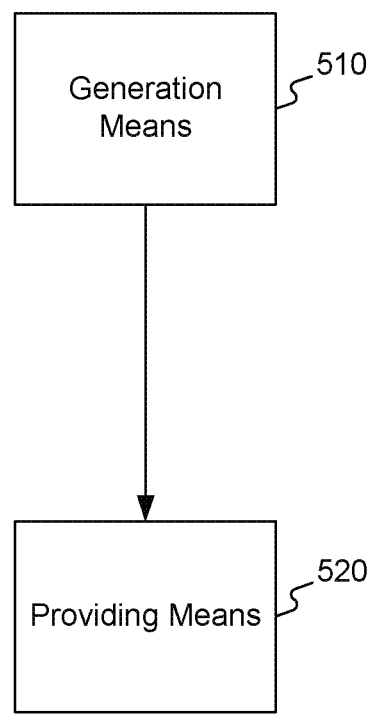
FIG. 5 depicts a block diagram illustrating exemplary functional components of a therapy unit.

As described above with reference to FIG. 3, in some embodiments the disclosed methods and systems may be implemented using therapy unit 330. FIG. 5 depicts a block diagram illustrating exemplary functional components of therapy unit 330, consistent with disclosed embodiments. In some embodiments, therapy unit 330 may comprise means for generating and means for providing therapeutic auditory stimulation. Means for generating the signal 510 may include one or more electronics devices. For example, generating means 510 may include a computer, such as a smartphone, tablet, laptop, desktop, or mainframe. As previously described with reference to FIG. 1, such a computer may comprise a processor and a non-transitory memory, such as a hard disk drive, solid state memory, on-board cache, or other memory. In some embodiments, the computer may receive instructions for generating the stimulation signal through an input/output interface or a network interface. For example, the computer may receive a computer program that configures the computer to generate the signal. Additionally or alternatively, the computer may receive parameters used by a computer program to configure the computer to generate the signal. The received parameters may comprise values or indications of values. For example, the computer may receive an indication that a user has interacted with a graphical user interface to select or configure certain therapeutic auditory stimulation. In some embodiments, generating means 510 may be incorporated into a medical product, such as a special-purpose diagnostic and therapeutic product intended to treat patients using the disclosed systems and methods.

Consistent with disclosed embodiments, the means for providing the signal 520 may obtain the stimulation signal from the generating means 510 and transduce the stimulation signal into therapeutic auditory stimulation. In some embodiments, the generation means and the providing means may together comprise a single device. In certain embodiments, a first device comprising the means for generating the stimulation signal may be distinct from a second device comprising the means for providing the therapeutic auditory stimulation. For example, the first device may be communicatively connected to the second device.

Providing means 520 may comprise local means for providing therapeutic auditory stimulation. Additionally or alternatively, the providing means may include remote means for providing the therapeutic auditory stimulation. In some embodiments remote providing means may include means for storing the stimulation signal. In certain embodiments, remote providing means may include means for transmitting the stimulation signal. Providing means 520 may include means for auditory therapy that converts the stimulation signal into therapeutic auditory stimulation.

Local providing means may include the contemporaneous and co-located generation and provision of the stimulation signal consistent with disclosed embodiments. Contemporaneous generation of the stimulation signal may include providing the signal as it is generated or provided the stimulation signal once generation of the signal is complete. Co-located stimulus signal generation may include generating the signal and providing the signal using the same device. For example, an electronics device, such as a music player, a computer, or a smartphone may both generate the stimulation signal and provide the stimulation signal for therapeutic auditory stimulation. As an additional example, a medical product, such as a special purpose therapeutic device, may generate and provide the stimulation signal.

Remote provide means may use means for storing the stimulation signal and means for transmitting the stimulation signal to enable a temporal or spatial separation between the generation of the stimulation signal and the provision of the therapeutic auditory stimulation. As a non-limiting example, the stimulation signal may be stored on a non-transitory computer-readable medium, such as the non-transitory memory described above. For example the signal may be stored on a compact disc, DVD, magnetic tape, disk drive, or flash memory, or similar storage medium. An analog signal or a digital signal may be stored. A digital signal may be stored as an audio file in any of a number of compressed or uncompressed file formats known to one of skill in the art.

In some embodiments, the signal may be stored as a sequence of values. These values may represent the amplitude of the signal. These values may be implicitly or explicitly associated with times. The values may correspond to or be derived from the amplitude of the signal as sampled at various points of time. In certain embodiments, the memory may store instructions for generating the signal. For example, the instructions may indicate a choice between pre-existing signals. Such pre-existing signals may be pre-programmed. As another example, the stored instructions may be parameters for use in generating the signal. For example, the parameters may be frequencies, durations, delays, amplitudes, rise or fall times, or other characteristics of signals consistent with disclosed embodiments.

Transmission means may permit the spatial separation of generation of the signal and the therapeutic use of the signal. In certain embodiments, the signal may be generated and then transmitted for therapeutic use. In some embodiments, the signal may be transmitted as the signal is being generated. Consistent with disclosed embodiments, the signal may be transmitted over a network, such as a cellular phone network, the public switched telephone network, or a computer network. The signal may also be transmitted stored in a computer-readable medium, such as a compact disc, DVD, flash memory, or audiotape. For example, an audio file containing the stimulation signal may be downloaded or streamed over a computer network from a server to a music player. As another example, the stimulation signal may be received at a telephone during a telephone call. As an additional example, the stimulation signal may be received as an attachment to message or email sent to a computer or a phone, such as a smartphone.

Audio therapy means may convert the stimulation signal into therapeutic auditory stimulation using any transduction method known to one of skill in the art. For example, audio therapy means may comprise audio speakers that convert a stimulation signal into therapeutic auditory stimulation. Consistent with disclosed embodiments, such audio speakers may be incorporated into electronics devices. For example, electronics devices may include consumer electronics capable of playing music, such as music players, computers, or telephones. Electronics devices may include medical devices, such as special-purpose diagnostic and therapeutic devices intended to treat patients using the disclosed systems and methods. The audio therapy means may be configured to produce audible therapeutic auditory stimulation with amplitude less than 50 decibels. Preferably, the amplitude of therapeutic auditory stimulation may range between 20-40 decibels.

Consistent with disclosed embodiments, therapeutic auditory stimulation may be provided repeatedly according to a stimulation regime. The stimulation regime may prescribe an initial treatment phase and a booster phase. Each phase may comprise stimulation sessions provided over a time period of multiple weeks. Stimulation sessions may be provided more frequently in the initial treatment phase than in the booster phase. Preferably, stimulation sessions may be provided every other day. More preferably, stimulation sessions may be provided 5 times during a two week block. During the booster phase, sessions of therapeutic auditory stimulation may be separated by multiple weeks.

In some embodiments, the initial treatment phase may be divided into blocks, separated by assessment intervals. During each block, stimulation sessions may be provided. During assessment intervals the effects of stimulation may be assessed. As described above, assessment may comprise the administration of diagnostic questionnaires or interviews.

In some embodiments, parameters of therapeutic auditory stimulation may be held constant between sessions. In certain embodiments, therapeutic auditory stimulation parameters may vary between sessions based on the effectiveness of the current stimulation parameters.

Figure 6A:
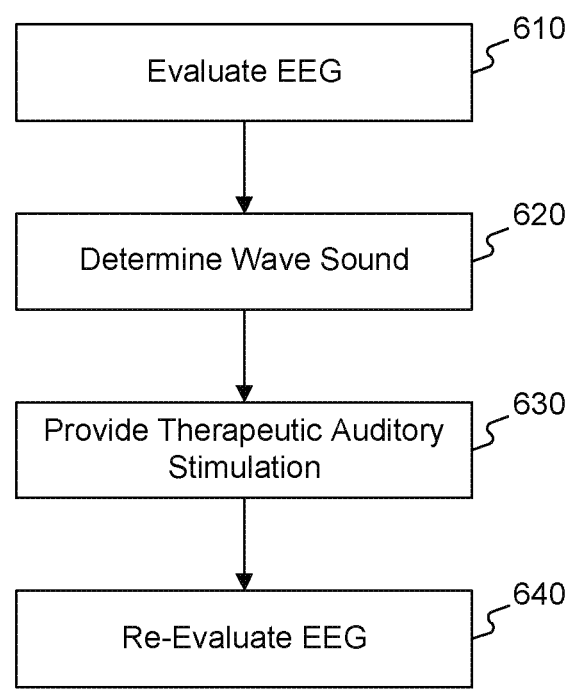
FIG. 6A depicts an exemplary method for providing therapeutic auditory stimulation.

FIG. 6A depicts an exemplary method for providing therapeutic auditory stimulation, consistent with disclosed embodiments. One of skill in the art would recognize that the particular order and sequence of events may be altered and is not intended to be limiting. Furthermore, steps may be removed or added without departing from the envisioned embodiments. For example, the sequence of steps depicted in FIG. 6 may be preferable for initially determining effective therapeutic auditory stimulation. Consistent with disclosed embodiments, subsequent stimulation sessions include only a subset of the steps shown in FIG. 6A, such as one or more instances of providing auditory stimulation.

Consistent with disclosed embodiments diagnostic unit 310 may be used to register the electroencephalogram of a patient (step 610). The process of registering the electroencephalogram of a patient is well known in the art and is included for completeness of description. In some embodiments, registering the EEG may involve multiple trials. In aspects, one or more trials may be conducted to establish a baseline EEG. For example, a first trial may be conducted with the patient's eyes open. A second trial may be conducted with the patient's eyes closed. In certain aspects, these trials may last one minute.

While these trials are conducted, the diagnostic unit may record EEG data and values extracted from the EEG data. For example, with reference to FIG. 4 discussed above, the diagnostic unit may store the data received by the signal processing unit 420. As an additional non-limiting example, signal processing unit 420 may store the results of transforming the received data, such as the signal powers for EEG bands, or the contribution of one or more EEG signal bands to the total power for the signal. As a further example, the diagnostic unit may store heart rate data received by the signal processing unit 420. As a non-limiting example, diagnostic unit 310 may store transformed heart rate data, such as the ratio of the low frequency components to the high frequency components of the power spectrum.

In some embodiments, diagnostics unit 310 may display, or provide for display, some or all of the stored data. A healthcare practitioner may use diagnostic unit 310 to assess the electroencephalogram of the patient. The healthcare practitioner may be, without limitation, a doctor, nurse, physician's assistant, therapist, psychologist, or other individual that provides patient care. In other embodiments, diagnostic unit 310 may be configured to automatically determine appropriate therapeutic auditory stimulation. In further embodiments, the patient may interact with diagnostic unit 310 to determine appropriate auditory stimulation.

Figure 6B:
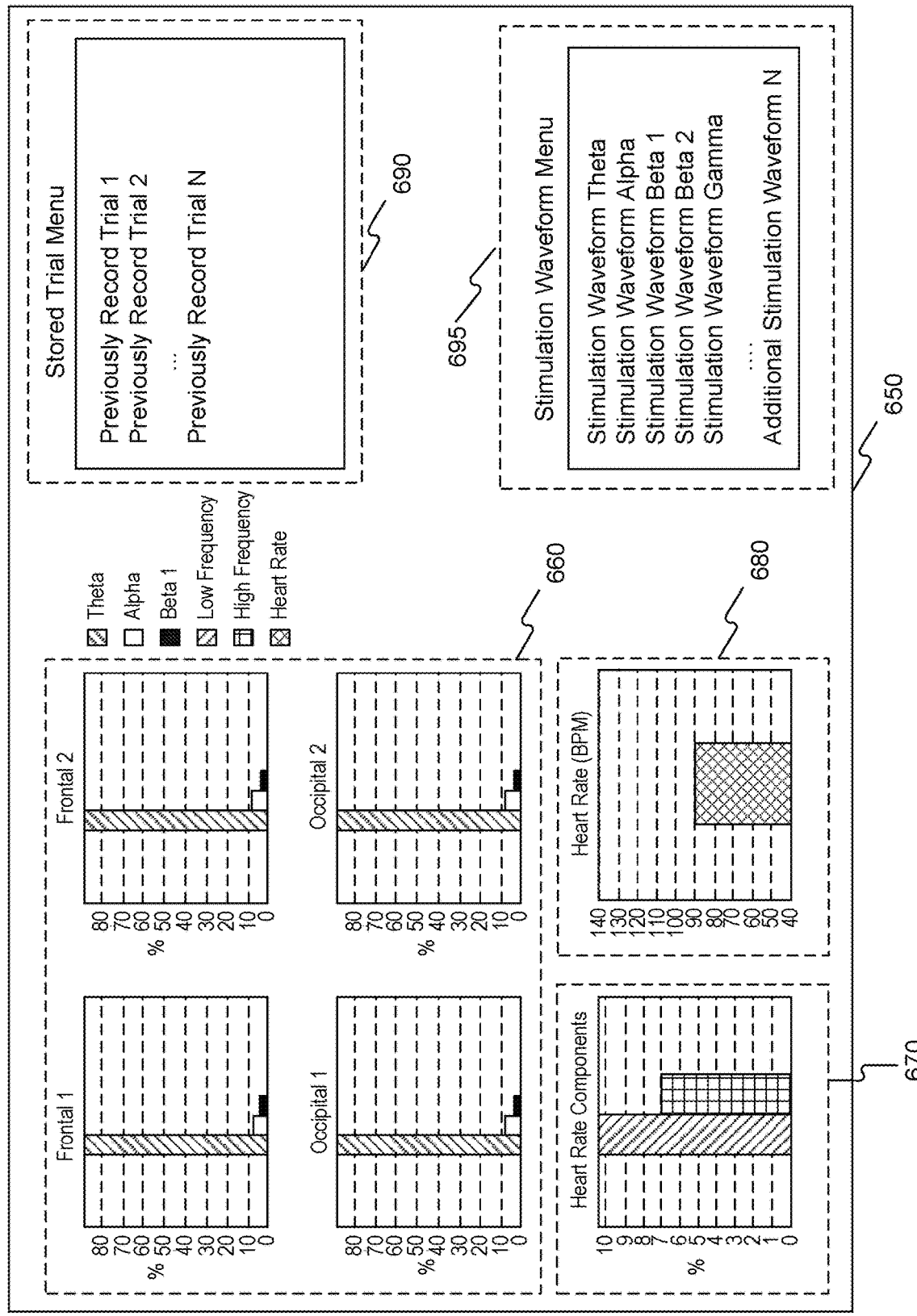
FIG. 6B depicts an exemplary user interface for providing therapeutic auditory stimulation.

FIG. 6B depicts an exemplary illustration of a user interface 650 for providing therapeutic auditory stimulation. User interface 650 may include EEG graphs 660 corresponding to each of frontal electrodes 412 and occipital electrodes 414. EEG Graphs 660 may display the contribution of one or more EEG bands to the overall signal power measured at each of the electrodes. Heart rate graph 670 may display the average heart rate of the patient during the trial. Heart rate variability graph 680 may show the relative contributions of the low and high frequency components of the heart rate to the overall signal power of the heat rate. Previously stored trials may be accessed through stored trial menu 690. Individual stimulation waveforms may be selected through stimulation waveform menu 695. As would be recognized by one of skill in the art, user interface 650 may be configured such that simulation waveforms may be provided by interacting with stimulation waveform menu 695, or another component of user interface 650.

Consistent with disclosed embodiments, appropriate therapeutic auditory stimulation may be determined in step 620. In certain aspects, this determination may be based on the results provided by diagnostic unit 310. In some embodiments, the determination may be based on the identification of abnormal EEG results, such as EEG results deviating from the typical or expected results for the patient, based on one or more of the age, present condition, and medical history of the patent. In some instances, the patient may exhibit an elevated contribution to total EEG signal power from one or more EEG bands. For example, the patient may exhibit minimal or abnormally low contributions of a first EEG band. This low contribution may imply an excessive contribution from another EEG band.

The determination of appropriate therapeutic auditory stimulation in step 620 may additionally or alternatively depend on other diagnostic criteria. In some embodiments, step 610 may comprise receiving the results of a diagnostic test. In certain aspects, this diagnostic test may involve an anatomical or physiological parameter of the patient. As a non-limiting example, the diagnostic test may comprise clinical laboratory test, such as a test performed in an anatomic pathology laboratory or a clinical pathology laboratory. In some embodiments, a healthcare practitioner may evaluate the patient using a questionnaire or assessment. In certain aspects, this questionnaire or assessment may be global, such as Clinical Global Impression-Severity and Improvement, Comprehensive Psychopathological Rating Scale, Global Assessment of Functioning, Children's Global Assessment Scale, or similar rating scale and/or assessment.

Additionally or alternatively, a healthcare practitioner may evaluate the patient using a questionnaire or assessment specific to a mental or psychological disorder. As a non-limiting example, a healthcare practitioner may evaluate the ADHD status of the patient using the Adult ADHD Self-Report Scale, Brown Attention Deficit Disorder Scales, Swanson, Nolan and Pelham Teacher and Parent Rating Scale, Vanderbilt ADHD Diagnostic Rating Scale, ADHD Rating Scale, or similar rating scales and/or assessments. As a further non-limiting example, a healthcare practitioner may evaluate the Autism spectrum status of the patient using the Adult Asperger Assessment, Australian scale for Asperger's syndrome, Autism Spectrum Quotient, Childhood Autism Rating Scale, Childhood Autism Spectrum Test, Q-CHAT, Autism Diagnostic Observation Schedule, or similar rating scales and/or assessments. As an additional non-limiting example, a healthcare practitioner may evaluate the patient for anxiety disorders using the Pediatric Anxiety Rating Scale, Child Anxiety Impact Scale, the Screen for Child Anxiety Related Emotional Disorders, the Brief Family Assessment Measure-III, and the Sleep Disturbance Scale, Beck Anxiety Inventory, Clinician Administered PTSD Scale, Daily Assessment of Symptoms—Anxiety, Generalized Anxiety Disorder 7, Hamilton Anxiety Scale, Hospital Anxiety and Depression Scale, Panic and Agoraphobia Scale, Panic Disorder Severity Scale, PTSD Symptom Scale—Self-Report Version, Social Phobia Inventory, Trauma Screening Questionnaire, Yale-Brown Obsessive Compulsive Scale, Zung Self-Rating Anxiety Scale, or similar rating scales and/or assessments. As an additional non-limiting example, a healthcare practitioner may evaluate the patient for dementia using the Abbreviated mental test score, Clinical Dementia Rating, General Practitioner Assessment Of Cognition, Informant Questionnaire on Cognitive Decline in the Elderly, Mini-mental state examination, or similar rating scales and/or assessments. As an additional non-limiting example, a healthcare practitioner may evaluate the patient for depression using the Beck Depression Inventory, Beck Hopelessness Scale, Centre for Epidemiological Studies—Depression Scale, Edinburgh Postnatal Depression Scale, Geriatric Depression Scale, Hamilton Rating Scale for Depression, Hospital Anxiety and Depression Scale, Kutcher Adolescent Depression Scale, Major Depression Inventory, Montgomery-Asberg Depression Rating Scale, Zung Self-Rating Depression Scale, or similar rating scales and/or assessments. As an additional non-limiting example, a healthcare practitioner may evaluate the patient for other psychological disorders using the Altman Self-Rating Mania Scale, Young Mania Rating Scale, Buss-Perry Aggression Questionnaire, Hare Psychopathy Checklist, Minnesota Multiphasic Personality Inventory or similar rating scales and/or assessments.

As would be recognized by one of skill in the art, a healthcare practitioner may evaluate the patient additionally or alternatively using guided or semi-structured interviews, such as the Anxiety Disorders Interview Schedule for DSM-IV, Research and Lifetime Version for Children and Parents. Self-reporting may also be used to gauge the incidence and severity of adverse behaviors, such as self-harm, or the occurrence of general health problems.

As an additional example, a healthcare practitioner may evaluate the patient using a questionnaire or assessment specific to an anatomical or physiological disorder. For example, a healthcare practitioner may evaluate the patient for Parkinson's using one or more of the International Parkinson and Movement Disorder Society diagnostic questionnaires, as would be understood by one of skill in the art. Additionally, consistent with disclosed embodiments, such questionnaires may be used in the diagnosis of headache and migraine, constipation, diabetes, cerebral palsy, stuttering, psychosomatic disorders, and pain disorders, as would be understood by one of skill in the art.

In some embodiments, the determination of appropriate therapeutic auditory stimulation in step 620 may depend on diagnostic tests conducted as part of a therapeutic auditory stimulation session. For example, the diagnostic test may be conduct during a therapeutic auditory stimulation session prior to provision of the therapeutic auditory stimulation. In certain embodiments, appropriate therapeutic auditory stimulation may be determined based on results of one or more previously conducted diagnostic test. In certain aspects, diagnostic unit 310 may be configured to determine appropriate therapeutic auditory stimulation based on the results of the diagnostic test. In some aspects, a healthcare practitioner may determine appropriate therapeutic auditory stimulation based on the results of the diagnostic test. In some aspects, the healthcare practitioner may interact with diagnostic unit 310 to determine appropriate therapeutic auditory stimulation based on the results of the diagnostic test.

As described in greater detail with reference to FIG. 7A-7D below, therapeutic auditory stimulation may comprise one or more stimulation waveforms. In certain aspects, the one or more stimulation waveforms may correspond to the excessively contributing EEG band. In certain instances, each of the EEG bands may contribute equally to the EEG power signal. In certain aspects, the appropriate therapeutic auditory stimulation may include one or more stimulation waveforms corresponding to a midrange EEG band. Consistent with disclosed embodiment, an EEG band defined with reference to a first EGG frequency and a second EEG frequency may correspond to a stimulation waveform having a first frequency associated with the first EEG frequency and a second frequency associated with the second EEG frequency. For example, the first EEG frequency may equal the first stimulation waveform frequency. As another example, the second EEG frequency may equal the second stimulation waveform frequency.

In some embodiments, the therapeutic auditory stimulation may comprise a train of stimulation waveforms. In certain aspects, the first stimulation waveform in the train may correspond to the excessively contributing EEG band. In various aspects, the first stimulation waveform may correspond to a chosen midrange EEG band. In some embodiments, subsequent stimulation waveforms in the train may correspond to progressively higher frequency EEG bands. In other embodiments, subsequent waveforms may correspond to progressively lower frequency EEG bands. For example, one or more stimulation waveforms may correspond to the theta EEG band. These stimulation waveforms may comprise a modulating waveform corresponding to the Theta EEG band. In one aspect, the modulating waveform may have a frequency that changes between 4 Hz and 7 Hz, in accordance with frequency boundaries of the theta EEG band.

In various embodiments, determination of the stimulation waveform may additionally or alternatively consider the heart rate and the heart rate variability of the patient. For example, the appropriate therapeutic stimulation may depend on the relative values of the low frequency component of the heart rate variability and the high frequency component of the heart rate variability. In some aspects, the appropriate therapeutic stimulation may include an initial stimulation waveform corresponding to a low EEG band when the low frequency component of the heart rate is less than the high frequency component of the heart rate. In various aspects the appropriate therapeutic stimulation may include an initial stimulation waveform corresponding to a high EEG band when the low frequency component of the heart rate is greater than the high frequency component of the heart rate.

As described with reference to step 610, in various embodiments the healthcare practitioner, diagnostic unit 310, or patient may determine the appropriate therapeutic auditory stimulation. In some embodiments, this determination may be made with reference to the displayed results of diagnostic unit 310.

TABLE 1

Stimulation Signals for Different Combinations of EEG Frequency Band Contributions and Heart Rate Variability (Eyes Closed). Table 1 depicts a non-limiting example of the stimulation waveforms comprising the appropriate therapeutic auditory stimulation for different combinations of results provided by diagnostic unit 310. The first four columns indicate the percentage of the total spectral density respectively contributed by the theta, alpha, beta 1, and beta 2 EEG frequency bands.

| % theta | % alpha | % beta 1 | % beta 2 | SVB ratio | Stimulation. Signal |
|---|---|---|---|---|---|
| >20 | <60 | <10 | <10 | LF < HF | Delta, Theta, Alpha |
| >10 | >60 | <20 | <10 | LF <= HF | Theta, Alpha, Beta 1 |
| <20 | <60 | >10 | >10 | LF >= HF | Alpha, Beta 1, Beta 2 |
| <10 | >20 | <60 | >10 | LF > HF | Beta 1, Beta 2, Gamma |

The fifth column indicates the relative contribution of the high and low frequency components of the heart rate variability. The sixth column indicates an appropriate corresponding stimulation signal for therapeutic auditory stimulation comprising a sequence of stimulation waveforms. The values in this table are for measurements conducted with the patient's eyes closed. The correspondence defined by this table may be acceptable for many of the conditions described above. For example, this correspondence may be used when treating depression, anxiety, pain, dementia, and autism spectrum disorders. As would be understood by one of skill in the art, this table non-limiting and provided for illustrative purposes.

Consistent with disclosed embodiments, therapeutic unit 330 may be configured to provide the appropriate therapeutic stimulation in step 630. In some embodiments, therapeutic unit 330 may be configured automatically by diagnostic unit 310. In various embodiments, therapeutic unit 330 may be configured by the healthcare practitioner. In certain embodiments, therapeutic unit 330 may be configured by the patient.

In some aspects, configuring therapeutic unit 330 may comprise selecting one or more stimulation waveforms. In some instances stimulation waveforms may be selected by interacting with a graphical user interface. In some embodiments, therapeutic unit 330 may be used repeatedly following selection of a stimulation regime. In other embodiments, therapeutic unit 330 may require selection of each stimulation waveform comprising the therapeutic auditory stimulation. For example, the patient or healthcare practitioner may need to select the next stimulation waveform once the current stimulation waveform has completed. In certain aspects, configuring therapeutic unit 330 may comprise providing parameters defining the stimulation waveform. Such parameters may define, as a non-limiting example, the amplitude of auditory stimulation, the number of stimulation waveforms provided, the EEG band corresponding to each stimulation waveform, frequencies of the stimulation waveform, durations of the stimulation waveform, and the nature of any components of the stimulation wave (as a non-limiting example, the numbering, ordering, and duration of components of the stimulation waveform).

As described in greater detail below, with respect to FIGS. 7A-7D, the duration of therapeutic auditory stimulation may vary. In some embodiments, this duration may depend on the number of stimulation waveforms comprising the therapeutic auditory stimulation. In other embodiments, the duration of the therapeutic auditory stimulation may depend on the duration of the stimulation waveforms. Preferably, the duration of the stimulation waveforms may be between 180 and 300 seconds. Preferably, the duration of the therapeutic auditory stimulation may be between 15 and 25 minutes. However, one of ordinary skill in the art would recognize that shorter or longer durations are possible for both the stimulation waveforms and the therapeutic auditory stimulation.

As described with respect to FIG. 5, therapy unit 330 may comprise means for generating stimulation signals and means for providing stimulation signals. The means for providing stimulation signal may include local means for providing stimulation signals. The means for providing stimulation signals may include remote means for providing stimulation signals. Remote means for providing stimulation signals may include transmission means or storage means for spatially and/or temporally separating the generation of the stimulation signals from the provision of the therapeutic auditory stimulation. According to the envisioned methods and systems, the structures and functions of diagnostic unit 310 and therapeutic unit 330 may be distributed among one or more devices.

Consistent with disclosed embodiments, diagnostic unit 310 may be used to re-assess the electroencephalogram of the patient following provision of therapeutic auditory stimulation. In some embodiments, this reassessment may comprise re-registering the EEG. The EEG may be registered with the patient's eyes open. Additionally, the EEG may be re-registered with the patients eyes closed. The diagnostic device 310 may store the EEG waveforms recorded during re-registration. The diagnostic device may display, or provide for display, the signals received by signal processing 420. The diagnostic device may display, or provide for display, the signals generated by signal processing 420. Based on the results of the re-registration, the therapeutic stimulation regime may be selected. In some embodiments, the healthcare practitioner may select the stimulation regime. In certain embodiments, the diagnostic unit 310 may select the stimulation regime. In various embodiments, the patient may select the stimulation regime.

In some embodiments, once the stimulation regime is selected, the patient may be enabled to provide themselves therapeutic auditory stimulation. In certain aspects, the patient may be provided a computer-readable medium storing the therapeutic auditory stimulation. In various aspects, the patent may be provided a device that generates and provides the therapeutic auditory stimulation. In some aspects, the patient may be granted access to a device that generates the therapeutic auditory stimulation. For example, the patient may be enabled to contact a device over a network, such as a telephone or computer network and receive the therapeutic auditory stimulation from the device over the network. As an additional example, the patient may listen to the therapeutic auditory stimulation over a telephone connection. In some embodiments, the patient may visit a healthcare practitioner to receive the therapeutic auditory stimulation.

FIGS. 7A-7D illustrate characteristics of exemplary waveforms for therapeutic auditory stimulation, consistent with disclosed embodiments. As discussed above with respect to FIG. 3 and FIG. 5, therapy unit 330 may comprise means for generating the stimulation signal. Therapy unit 330 may also comprise means for providing the signal and converting the stimulation signal into therapeutic auditory stimulation.

Figure 7A:
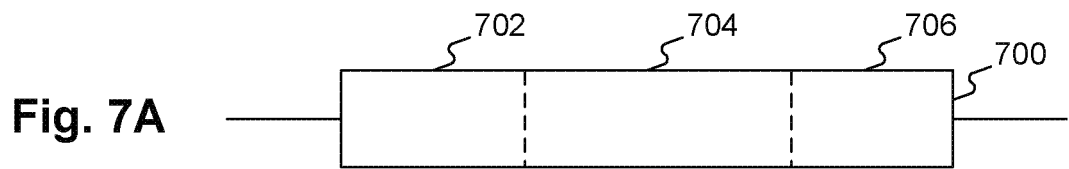
FIGS. 7A-7D depict characteristics of exemplary waveforms for therapeutic auditory stimulation.

As shown in FIG. 7A, stimulation signal 700 may comprise one or more stimulation waveforms consistent with disclosed embodiments. In some embodiments, first waveform 702, second waveform 704, and third waveform 706 may comprise a train of waveforms. In certain embodiments, an interval of time may separate one or more adjacent stimulation waveforms, such as first stimulation waveform 702 and second waveform 704. For example, first stimulation waveform 702 may first be selected and provided and then second stimulation waveform 704 may next be selected and provided. In other embodiments, no interval of time may separate adjacent stimulation waveforms. In some embodiments, the waveforms may differ in at least one or more of amplitude, duration, or frequency. The disclosed embodiments are not limited to stimulation signals comprising three waveforms: one of skill in the art would recognize that a lesser or a greater number of stimulation waveforms may be included in stimulation signal 700.

Consistent with disclosed embodiments, stimulation waveforms may correspond to EEG bands. As described above, this correspondence may be based on the therapeutic effect of the stimulation waveform. For example, providing a stimulation waveform as therapeutic auditory stimulation may cause a decrease in the power spectral density contribution of the corresponding EEG band of an EEG signal received from the signal conditioning unit 410. This change in the corresponding EEG band may be correlated with a subjective or objective change in the mental state of the patient. For example, a stimulation waveform comprising a modulating waveform with a frequency between 4 Hz and 7 Hz may correspond to the theta EEG band. Providing such a stimulation waveform as therapeutic auditory stimulation may reduce the proportional contribution of the theta EEG band to the power spectral density of an EEG signal received from the signal conditioning unit 410.

As described above with respect to FIG. 2A, a collection of two or more EEG frequency bands may include a high-frequency band and a low-frequency band. In some embodiments, stimulation signal 700 may include a stimulation waveform corresponding to a low-frequency band before a stimulation waveform corresponding to a high-frequency band. For example, in some embodiments, stimulation signal 700 may include stimulation waveforms corresponding to progressively higher EEG frequency bands. For example, first stimulation waveform 702 may correspond to the Delta EEG band, second stimulation waveform 704 may correspond to the Theta EEG band, and third stimulation waveform may correspond to a Beta EEG band. Providing stimulation waveforms of progressively higher amplitude may increase the proportional contribution of higher frequency EEG bands to the power spectral density of the EEG signal received from signal conditioning unit 410. In certain embodiments, stimulation signal 700 may include a stimulation signal corresponding to a high-frequency band before a stimulation signal corresponding to a low frequency band. For example, stimulation signal 700 may include stimulation waveforms corresponding to progressively lower EEG frequency bands. As would be recognized by one of skill in the art, the exact progression of stimulation waveforms would depend on the patient's diagnosis.

Stimulation waveforms, such as stimulation waveform 702, may comprise one or more carrier waveforms consistent with disclosed embodiments. In some embodiments, this carrier waveform may be audible. In certain embodiments, the carrier waveform may be periodic. As a non-limiting example, the carrier waveform may approximate a sinusoidal waveform. In various embodiments, the carrier waveform may have a fundamental frequency within the audible range. For example, the carrier waveform may have a frequency between 100 Hz and 20 kHz. Preferably, the fundamental frequency of the carrier waveform may be between 500 Hz and 5 kHz. More preferably, the frequency of the carrier waveform may be approximately 1 kHz.

A modulating waveform may modulate the carrier waveform consistent with disclosed embodiments. In some embodiments, the modulating waveform may have a non-zero frequency. In certain embodiments, this frequency may vary non-linearly with time. For example, the modulating signal may have an instantaneous frequency that varies exponentially with time. As an additional example, the instantaneous frequency of a stimulation waveform (such as stimulation waveform 702) may increase and decrease exponentially over the duration of the stimulation waveform. For example, the instantaneous frequency may increase to a maximum frequency and decrease to a minimum frequency. In some embodiments maximum and minimum frequency for the EEG band corresponding to the stimulation waveform may be the maximum and minimum instantaneous frequency of the modulating waveform. For example, the maximum instantaneous frequency for a stimulation waveform corresponding to a theta EEG band may be 13 Hz, when 13 Hz is taken to define the maximum frequency of the theta EEG band.

Figure 7B:
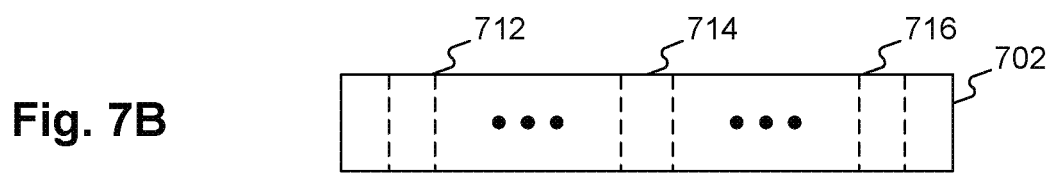

As shown in FIG. 7B, stimulation waveforms, such as stimulation waveform 702, may comprise pairs of frequency intervals, such as 712, 714 or 716, consistent with disclosed embodiments. In some embodiments, these frequency interval pairs may differ in duration. In certain embodiments, an interval of time may separate one or more adjacent frequency interval pairs, such as frequency interval pair 712 and frequency interval pair 714. In other embodiments, no interval of time may separate adjacent frequency interval pairs. During each frequency interval pair, the instantaneous frequency of the modulating signal may vary non-linearly between the maximum and minimum instantaneous frequency for that stimulation waveform. For example, during a frequency interval pair, the instantaneous frequency may increase exponentially from the minimum frequency to the maximum frequency and then decease exponentially back to the minimum frequency. The number of frequency interval pairs in a stimulation waveform may range from 4 to 12 pairs. Preferably, the number of stimulation interval pairs may range from 7 to 10 pairs.

In certain embodiments, stimulation waveforms may include only one interval. Over that interval, the instantaneous frequency of the modulating signal may vary non-linearly. The instantaneous frequency of the modulating signal may increase from the minimum to the maximum instantaneous frequency for that stimulation waveform. The instantaneous frequency of the modulating signal may decrease from the maximum to the minimum instantaneous frequency for that stimulation waveform.

Figure 7C:
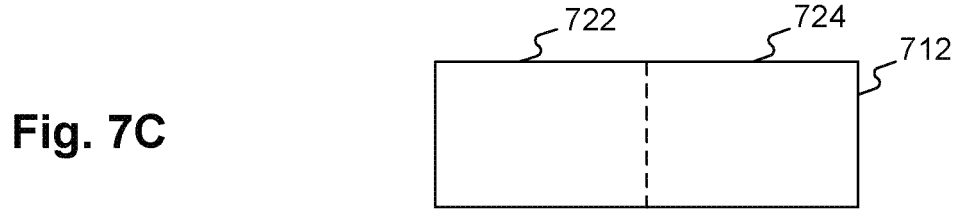

As shown in FIG. 7C, frequency interval pairs, such as frequency interval pair 712, may comprise frequency intervals. In certain aspects, frequency interval pairs may comprise increasing frequency intervals (such as 722) and decreasing frequency intervals (such as 724). In some embodiments, the increasing frequency interval may precede the decreasing frequency interval in a frequency interval pair. In certain embodiments, an interval of time may separate the increasing and decreasing frequency intervals in one or more frequency interval pairs. In other embodiments, no interval of time separates increasing and decreasing frequency intervals.

The instantaneous frequency of the modulating waveform may increase non-linearly during the increasing frequency interval consistent with disclosed embodiments. For example, the instantaneous frequency of the modulating waveform may increase exponentially from the minimum frequency to the maximum frequency of the stimulation waveform during the increasing stimulation interval. In certain embodiments, the instantaneous frequency of the modulating waveform may decrease non-linearly during the decreasing frequency interval. For example, the instantaneous frequency of the modulating waveform may decrease exponentially from the maximum frequency to the minimum frequency of the stimulation waveform during the decreasing stimulation interval.

The duration of the increasing and decreasing frequency intervals comprising a frequency interval pair in a stimulation waveform may depend on the EEG bands, consistent with disclosed embodiments. In some embodiments, these durations may be selected based on the minimum and maximum frequencies defining certain of the EEG bands. For example, the selected durations may equal a number of seconds corresponding to one of the minimum or maximum frequencies, expressed in hertz. In some instances, the certain EEG bands may be near in frequency to the EEG band corresponding to the stimulation waveform. For example, the durations of the increasing and decreasing frequency intervals comprising the frequency interval pairs in a stimulation waveform corresponding to the alpha EEG band may be chosen from the minimum and maximum frequencies defining the alpha, delta, theta, and beta 1 EEG bands. Similarly, the durations of the increasing and decreasing frequency intervals comprising the frequency interval pairs in a stimulation waveform corresponding to the gamma EEG band may be chosen from the minimum and maximum frequencies defining the gamma, beta 2 and beta 1 EEG bands.

Consistent with disclosed embodiments, the durations of increasing and decreasing frequency intervals in a stimulation waveform may vary according to a pattern. In certain embodiments, the durations of the increasing and decreasing frequency intervals may progressively increase. For example, frequency interval pair 712 may comprise increasing frequency interval 722 with duration 8 seconds and decreasing frequency interval 724 with duration 13 seconds. In this example, frequency interval pair 714 may then comprise an increasing frequency interval with duration 13 seconds and a decreasing frequency interval with duration 21 seconds. In certain embodiments, the durations of the increasing and decreasing frequency intervals may progressively decrease. For example, frequency interval pair 712 may comprise increasing frequency interval 722 with duration 13 seconds and decreasing frequency interval 724 with duration 21 seconds. In this example, frequency interval pair 714 may then comprise an increasing frequency interval with duration 8 seconds and a decreasing frequency interval with duration 13 seconds. As shown in Table 2, in some embodiments, the duration of the increasing and decreasing frequency intervals may first increase and then decrease, or first decrease and then increase. In some embodiments, the duration of the decreasing frequency interval in a frequency interval pair exceeds the duration of the increasing frequency interval in the frequency interval pair.

TABLE 2

Exemplary Stimulation Waveforms. Each stimulation waveform is identified by a corresponding EEG band (alpha → gamma). The second and third columns show the maximum and minimum instantaneous frequencies of the modulating waveform for the stimulation waveform. The forth column shows the duration in seconds of the increasing and decreasing frequency intervals for each frequency interval pair in the stimulation waveform. The fifth column shows the total duration of the stimulus waveform in seconds. As one of skill in the art would appreciate, the exemplary stimulation waveforms depicted in Table 2 are not intended to be limiting.

| Corresponding EEG Band | Maximum Frequency (Hz) | Minimum Frequency (Hz) | Duration of Intervals (s) (increasing-decreasing) | Total Duration (s) |
|---|---|---|---|---|
| Alpha | 13 | 8 | 13-21, 8-13, 5-8, 3-5, 5-8, 8-13, 13-21, 8-13, 5-8, 3-5 | 186 |
| Theta | 8 | 5 | 13-21, 8-13, 5-8, 3-5, 5-8, 8-13, 13-21, 8-13, 5-8, 3-5 | 186 |
| Delta | 5 | 3 | 13-21, 8-13, 5-8, 3-5, 5-8, 8-13, 13-21, 8-13, 5-8, 3-5 | 186 |
| Beta 1 | 21 | 13 | 13-21, 8-13, 5-8, 3-5, 5-8, 8-13, 13-21, 8-13, 5-8, 3-5 | 186 |
| Beta 2 | 34 | 21 | 21-34, 13-21, 8-13, 13-21, 21-34, 13-21, 8-13 | 254 |
| Gamma | 55 | 34 | 34-55, 21-34, 13-21, 21-34, 34-55, 21-34, 13-21 | 254 |

In some embodiments, the duration of an interval may approximate be a constant multiple of the duration of a previous interval. In some embodiments, this multiple may approximate φ. In certain aspects, the duration of a decreasing interval in an interval pair may be an approximately constant multiple of the duration of the increasing interval in the interval pair. Table 2 provides non-limiting examples of stimulation waveforms with intervals meeting this duration criteria. For example, the stimulation waveform gamma includes a first increasing interval with duration 34 seconds, a first decreasing interval with duration 55 seconds (a ratio of 1.617), a second increasing interval with duration 21 seconds, and a second decreasing interval with duration 34 seconds (a ratio of 1.619), etc. In some aspects the ratio between an interval in a first pair and the corresponding interval in a second pair may approximate φ. As an additional example, the stimulation waveform gamma includes a first increasing interval of duration 34 second and a second increasing interval of duration 21 seconds (a ratio of 1.619).

Figure 7D:
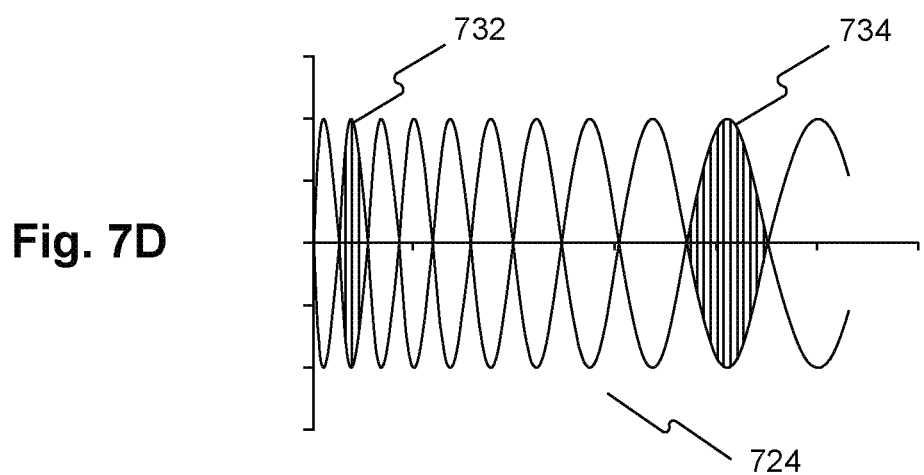

FIG. 7D shows a schematic of the amplitude-modulated carrier waveform consistent with disclosed embodiments. The schematic depicts the amplitude-modulated carrier waveform during a decreasing frequency interval, such as decreasing frequency interval 724. The modulating waveform defines the envelope of the amplitude-modulated carrier waveform, while the frequency carrier waveform is illustrated schematically at time 732 and 734. As shown at time 732 and 734, the frequency of the modulating waveform progressively decreases, while the frequency of the carrier waveform remains constant.

In some embodiments, the instantaneous frequency of the modulating waveform during an increasing frequency interval may be given as:

$$F_{mod}=F\min+(F\max-F\min)*(1-\exp(-5t/T\text{rise}))$$

Where $F_{mod}$ is the instantaneous frequency, $F_{min}$ is the minimum frequency of the stimulation waveform, Fmax is the maximum frequency of the stimulation waveform, and $T_{rise}$ is the rise time of the frequency. In some embodiments $T_{rise}$ may be the duration of the increasing frequency interval. In some embodiments, as shown above, the multiplier of t in the argument to the exponential may be −5. In certain aspects, the multiplier of t in the argument to the exponential may be selected from the range of [−7, −3]. In this manner the rapidity of the frequency change may be modulated to further reduce the likelihood of patient adaptation to the therapeutic auditory stimulation.

In some embodiments, the instantaneous frequency of the modulating waveform during a decreasing frequency interval may be given as:

$$F_{mod}=F\min+(F\max-F\min)*(1-\exp(-5t/T\text{rise}))$$

Where $F_{mod}$ is the instantaneous frequency, $F_{min}$ is the minimum frequency of the stimulation waveform, $F_{max}$ is the maximum frequency of the stimulation waveform, and $T_{rise}$ is the rise time of the frequency. In some embodiments, $T_{rise}$ may be the duration of the decreasing frequency interval. In some embodiments, as shown above, the multiplier of t in the argument to the exponential may be −5. In certain aspects, the multiplier of t in the in the argument to the exponential may be selected from the range of [−7, −3]. In certain aspects, the multiplier of t in the argument to the exponential may be selected from the range of [−7, −3]. In this manner the rapidity of the frequency change may be modulated to further reduce the likelihood of patient adaptation to the therapeutic auditory stimulation.

One of skill in the art would recognize that alternative stimulation signals may also be used. For example, in some embodiments, the stimulation signal may comprise multiple stimulation waveforms, each either increasing or decreasing in frequency. For each of these stimulation waveforms, the instantaneous frequency of the modulating signal may vary non-linearly from a first instantaneous frequency for that stimulation waveform to a second instantaneous frequency for that stimulation waveform. For example, a stimulation signal may comprise a first stimulation waveform corresponding to the alpha EEG band, a second stimulation waveform corresponding to the beta 1 EEG band, and a third stimulation waveform corresponding to the beta 2 EEG band, each of the stimulation waveforms having an increasing modulation waveform frequency. In such an example, the stimulation frequency will repeatedly increase in a nonlinear stepwise fashion. This stimulation signal could further the reverse sequence of stimulation waveforms, each having a decreasing modulation waveform frequency. Alternatively, the stimulation signal could repeat the sequence of stimulation waveforms, restarting with stimulation having the lowest instantaneous frequency of the first stimulation waveform. In some embodiments, the instantaneous frequency of the modulating waveform may vary linearly:

$$F_{mod}=F_{start}+(F_{finish}-F_{start})*(t/T_{duration})$$

Where $F_{mod}$ is the instantaneous frequency, $F_{start}$ is the frequency at the beginning of the increasing or decreasing frequency interval, $F_{finish}$ is the maximum frequency at the end of the increasing or decreasing frequency interval, and $T_{duration}$ is the duration over which the frequency changes linearly. In some embodiments, $T_{duration}$ may be the duration of the increasing or decreasing frequency interval. In various embodiments, the instantaneous frequency of the modulating waveform may cease changing once t is greater than $T_{duration}$.

In some embodiments, two or more waveforms may be combined to create stuffed stimulation waveform 702. For example, stuffed stimulation waveform 702 may comprise a first waveform corresponding to a first EEG band mixed with a second waveform corresponding to a second EEG band. In some aspects, stuffed stimulation waveform 702 may comprise one more waveforms generated and provided for therapeutic stimulation in a temporally overlapping manner. For example, a predetermined gap may separate the beginning of the first waveform and the beginning of the second waveform. As an additional example, a predetermined gap may separate the end of the first waveform and the end of the second waveform. In some aspects one or more waveforms may be generated simultaneously. For example, the first waveform and the second waveform may begin at the same time. As another example the first waveform and the second waveform may end at the same time. In some embodiments, to align the beginning and end of the one or more waveforms comprising a stuffed stimulation waveform 702, the duration of at least one of the one or more waveforms may be scaled. For example the duration of at least one of the increasing and decreasing frequency intervals in the at least one of the one or more waveforms may be multiplied by a scaling factor. In certain aspects multiple waveforms may be generated, mixed by an analog or digital mixer, and then provided for therapeutic stimulation. In various aspects, stuffed waveform 702 may be stored, retrieved, and then provided for therapeutic stimulation. In some aspects, stuffed waveform 702 may be generated by simultaneously providing one or more waveforms through multiple speakers, without mixing at least one of the one or more waveforms. Likewise, and in the same manner, in some embodiments one or more stimulation signals 700 may be combined to create stuffed stimulation signals 700.

Exemplary Therapeutic Auditory Stimulation Protocol

Consistent with disclosed embodiments, therapeutic auditory stimulation may be used to treat patients with autism spectrum disorders. In certain aspects, patients may receive a predetermined number of sessions of therapeutic auditory stimulation. For example, patients may receive between 2 and 20 sessions of therapeutic auditory stimulation. As an additional example, patients may receive between 8 and 14 sessions of therapeutic auditory stimulation. Sessions may be approximately daily, weekly, bimonthly, or monthly, or a combination of such intervals. For example, a first session may be followed by another session approximately a week later, which may be followed by another session approximately a day, week, two weeks, or month later. In some embodiments, patients may receive therapeutic auditory stimulation so long as they continue to exhibit symptoms. In certain embodiments, patients may receive therapeutic auditory stimulation as a maintenance therapy indefinitely.

In certain embodiments, patients may receive a predetermined stimulation signal. In certain aspects, this stimulation signal may include three stimulation waveforms. In some aspects this stimulation signal may include four stimulation waveforms. In some aspects this stimulation signal may include more than four stimulation waveforms, such as six stimulation waveforms. The duration of each stimulation waveform may vary. For example, the duration of the stimulation waveforms may vary between 1 and 10 minutes. The total duration of stimulation may vary between 10 and 30 minutes. In some aspects, within each stimulation signal, the stimulation waveforms may correspond to progressively increasing EEG frequency bands. Exemplary stimulation signals are provided in Table 3 below.

TABLE 3

Exemplary Stimulation Signals. Each row indicates an exemplary stimulation signal comprising either three or four stimulation waveforms. These stimulation waveforms may correspond to EEG frequency bands, for example the second stimulation waveform in the third signal may correspond to the Beta 2 EEG frequency band. The individual stimulation waveforms may comprise pairs of increasing and decreasing frequency intervals as described above with regard to FIGS., 7A-7D. The individual stimulation waveforms may include a modulation waveform that varies nonlinearly between a maximum and minimum frequency value. In certain aspects, the maximum and minimum frequency values may be the values listed in Table 2. In some embodiments, the stimulation signals in Table 3 may comprise a sequential course of therapeutic auditory stimulation. For example, patients may receive stimulation signals 1-12 in sequential sessions.

| Stimulation Signal | Stimulation Waveform 1 | Stimulation Waveform 2 | Stimulation Waveform 3 | Stimulation Waveform 4 |
|---|---|---|---|---|
| 1 | Alpha | Beta 1 | Beta 2 | None |
| 2 | Alpha | Beta 1 | Beta 2 | Gamma |
| 3 | Beta 1 | Beta 2 | Gamma | None |
| 4 | Alpha | Beta 1 | Beta 2 | None |
| 5 | Theta | Alpha | Beta 1 | Beta 2 |
| 6 | Theta | Alpha | Beta 1 | None |
| 7 | Delta | Theta | Alpha | Beta I |
| 8 | Delta | Theta | Alpha | None |
| 9 | Theta | Alpha | Beta 1 | None |
| 10 | Theta | Alpha | Beta 1 | Beta 2 |
| 11 | Alpha | Beta 1 | Beta 2 | Gamma |
| 12 | Beta 1 | Beta 2 | Gamma | None |

Therapeutic Auditory Stimulation—Case Studies

Figure 2C:
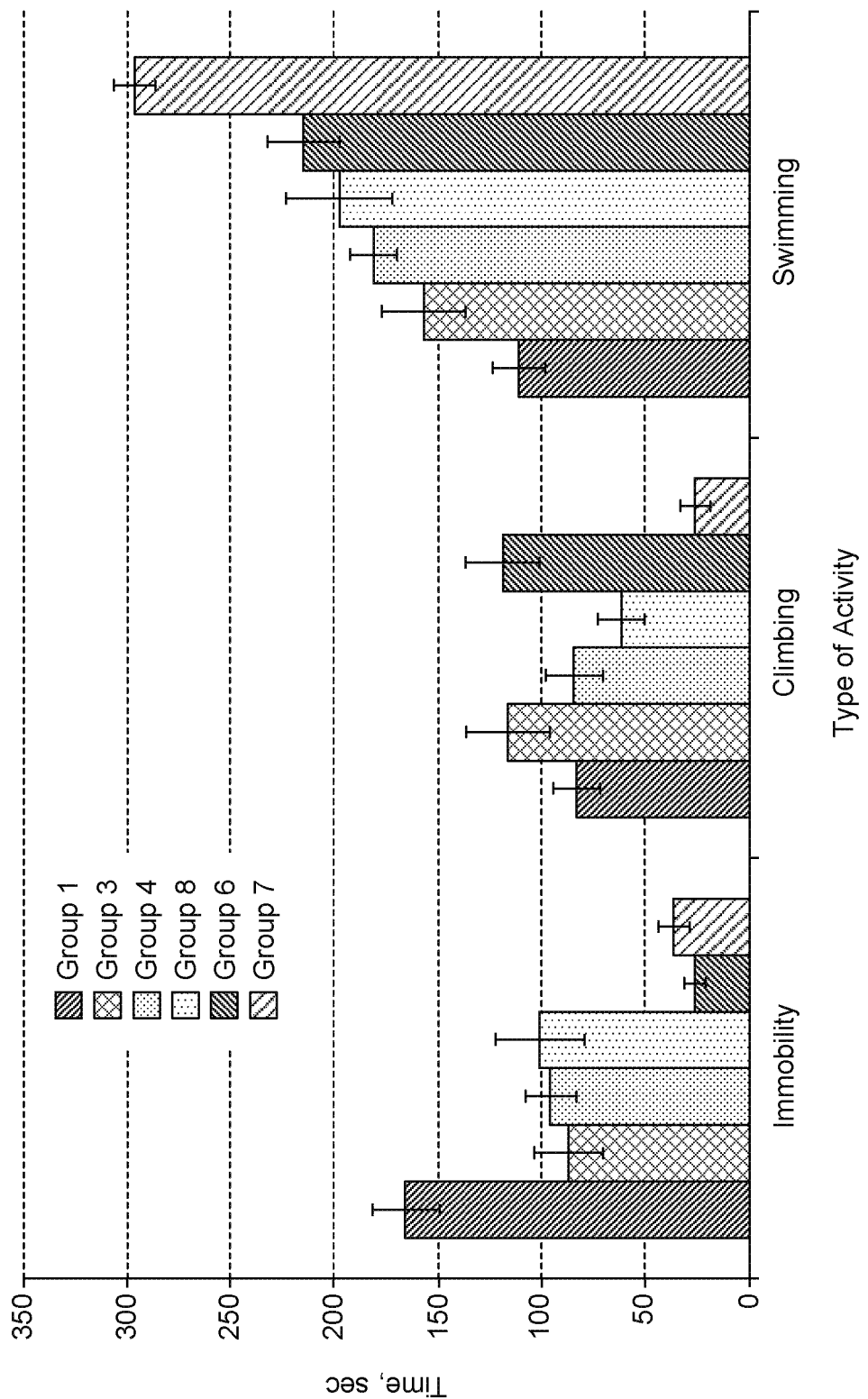
FIG. 2C depicts the effect of therapeutic auditory stimulation in a model of depression.

Beneficial results of simplified forms of therapeutic auditory stimulation have been observed in animals. For example, as reported in "Investigation of antidepressants activity of sound beats created with different algorithms of modulation in comparison with antidepressants in forced swim test (FST) on rats," cited above and hereby incorporated by reference in its entirety, therapeutic auditory stimulation has been shown to provide benefits in an animal model of depression. In this study, therapeutic auditory stimulation using an amplitude and frequency modulated 1 kHz carrier wave reduced immobility and increased swimming in rates during a forced swim test. These tests were conducted on 89 healthy rats divided into eight groups. Three groups served as controls: one received no treatment (Group 1), one received an unmodulated 1 kHz carrier wave (Group 2), and one received saline solution injections (Group 5). Two groups received auditory stimulation therapy consisting of amplitude and frequency modulated sounds at either 2-13 Hz (Group 3) or 13-55 Hz (Group 4). Three groups received known chemical antidepressants (Group 6—Amitriptyline; Group 7—Mianserin, and Group 8—Sertaline). As shown in FIG. 2C, the rats treated with the auditory stimulation therapy exhibited increased swimming and decreased immobility as compared to the intact control rats.

Therapeutic auditory stimulation consistent with the disclosed embodiments has also been shown to benefit human patients with anxiety, depression, and chronic pain. In one study, twenty-two patients suffering from severe depression and chronic pain, and four patients suffering from high anxiety received therapeutic auditory stimulation in two sessions approximately every other day. The patients provided a subjective assessment of the therapy after every session and after two weeks of treatment. Of the twenty-six patients, twenty-three experienced some reduction in symptoms. The four patients with high anxiety experienced a marked reduction in anxiety. Of the twenty-two patients with severe depression and chronic pain, nineteen experienced some reduction in symptoms.

Therapeutic auditory stimulation consistent with the disclosed embodiments has also been shown to benefit a patient diagnosed with Asperger's Syndrome. This patient received three sessions of therapeutic auditory stimulation a day for three days. The patient described a reduction in stress and anxiety from the therapeutic auditory stimulation. This self-report was corroborated by reports from the parents, teachers, and counselor of the patient.

Five autistic patients received therapeutic auditory stimulation consistent with disclosed embodiments. Pre-training baseline 19 channel EEG recordings were obtained prior to therapeutic auditory stimulation. Recorded EEG data was analyzed using quantitative topographic and LORETA tomographic analysis. Stimulation waveforms were chosen based on most abnormal EEG frequency band and most deviant Z score LORETA voxel. Stimulation was provided for approximately 10 minutes through audio speakers. Post-training baseline 19 channel EEG recordings were obtained following therapeutic auditory stimulation. Pre and post training comparisons were performed using paired t-tests and Cohen's d for effect sizes. The results are given in Table 4 below.

TABLE 4

Results of Therapeutic Auditory Stimulation for Five Autistic Patients. The most deviant Brodmann area, as determined using LORETA EEG, is listed in the second column, while the most deviant EEG frequency band is listed in the third column. The baseline Z score indicates the Z score of the most deviant voxel identified by LORETA EEG, while the Z score change towards normal indicates the change in this Z score following therapeutic auditory stimulation. The P value indicates the statistical significance of the change, while the effect size indicates the clinical magnitude of the change.

|  | Most Deviant Brodmann Area | Most Deviant EEG Frequency Band | Baseline Z Score | Z Score Change Toward Normal | P Value | Effect Size |
|---|---|---|---|---|---|---|
| Case 1 | 10 Right | Delta | +4.74 | 2.62 | P < 0.00001 | Very Large |
| Case 2 | 2 Left | Theta | +6.12 | 1.88 | P < 0.00001 | Very Large |

TABLE 4-continued

Results of Therapeutic Auditory Stimulation for Five Autistic Patients. The most deviant Brodmann area, as determined using LORETA EEG, is listed in the second column, while the most deviant EEG frequency band is listed in the third column. The baseline Z score indicates the Z score of the most deviant voxel identified by LORETA EEG, while the Z score change towards normal indicates the change in this Z score following therapeutic auditory stimulation. The P value indicates the statistical significance of the change, while the effect size indicates the clinical magnitude of the change.

|  | Most Deviant Brodmann Area | Most Deviant EEG Frequency Band | Baseline Z Score | Z Score Change Toward Normal | P Value | Effect Size |
|---|---|---|---|---|---|---|
| Case 3 | 24 Left | High Beta | +4.33 | 1.59 | P < 0.00001 | Very Large |
| Case 4 | 47 Right | Delta | +4.05 | 1.9 | P < 0.00001 | Very Large |
| Case 5 | 23 Left | Delta | +5.77 | 2.14 | P < 0.00001 | Very Large |

Figure 8B:
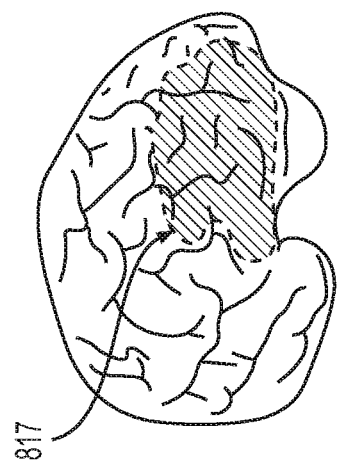
FIGS. 8A-8D depict exemplary pre-treatment and post-treatment neuroimages obtained using LORETA EEG that illustrate the effect of therapeutic auditory stimulation on abnormal neural activity.
Figure 8D:
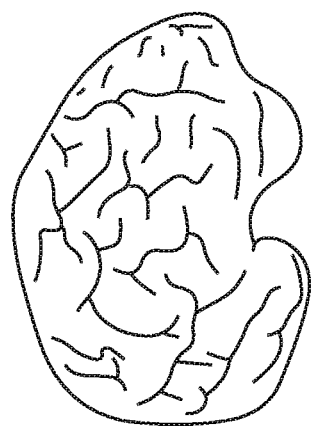
Figure 8A:
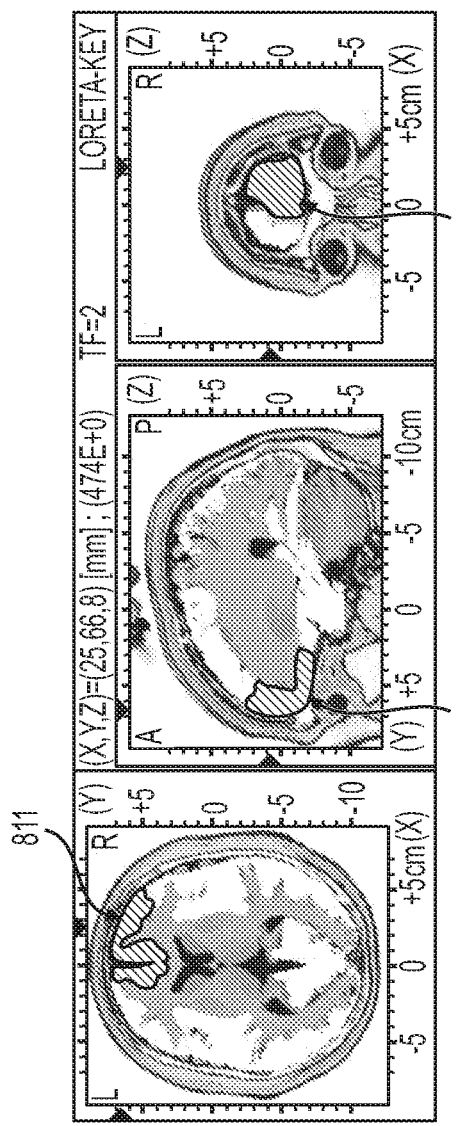
Figure 8C:
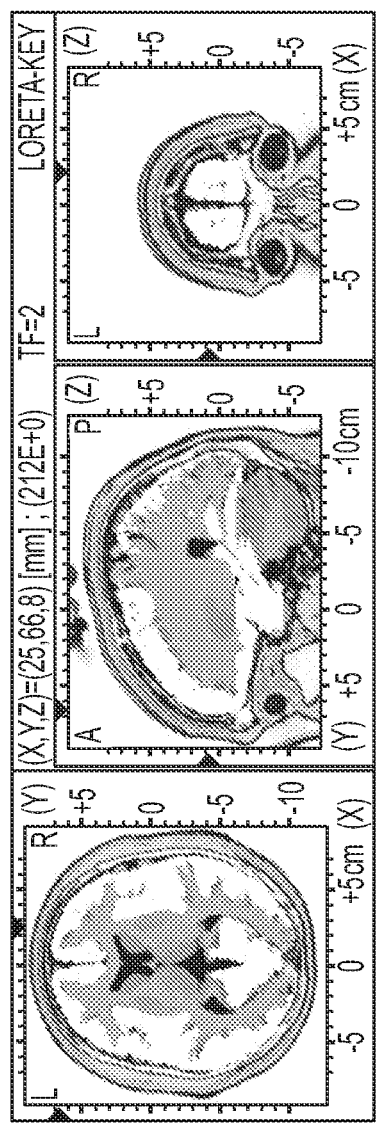

FIGS. 8A-8D depict the results of this intervention for Case 1. FIGS. 8A and 8B depict four neuroimages of the patient's brain during acquisition of the pre-therapy baseline EEG recording. As shown, the patient is experiencing an abnormal area of activation, shown by 811, 813, 815, and 817. FIGS. 8C and 8D depict the same four neuroimages of the patient's brain during acquisition of the post-therapy baseline EEG recording. As shown, following the 10 minutes of therapeutic auditory stimulation, the patient is no longer experiencing the abnormal activity depicted in FIGS. 8A and 8B. Similar results were seen with other cases in the study.

This study demonstrated that therapeutic auditory stimulation consistent with disclosed embodiments was able to disentrain or dehabituate abnormal and deregulated neural network activity. Thus this therapeutic auditory stimulation could be used to normalize neural function, relieve symptoms and improve system adaptivity. Dynamic analyses of specific frequency bands during stimulation also revealed frequency-band specific disentrainment effects.

Additionally, thirty-five patients with autism, Asperger's, attention deficit disorder, and anxiety disorders are currently being treated with therapeutic auditory stimulation as part of an ongoing clinical research project. Many of these patients have demonstrated a reduction in symptoms and noticeable improvements in functioning during treatment.

The foregoing description of the inventions, along with their associated embodiments, has been presented for purposes of illustration only. It is not exhaustive and does not limit the inventions to the precise form disclosed. Those skilled in the art will appreciate from the foregoing description that modifications and variations are possible in light of the above teachings or may be acquired from practicing the inventions. For example, the steps described need not be performed in the same sequence discussed or with the same degree of separation. Likewise various steps may be omitted, repeated, or combined, as necessary, to achieve the same or similar objectives. Similarly, the systems described need not necessarily include all parts described in the embodiments, and may also include other parts not describe in the embodiments. Accordingly, the inventions are not limited to the above-described embodiments, but instead are defined by the appended claims in light of their full scope of equivalents.

What is claimed is:

1. A device for providing therapeutic visual stimulation comprising:
a processor and a non-transitory memory containing instructions that when executed by the processor cause the device to generate one or more stimulation waveforms, the one or more stimulation waveforms:
corresponding to electroencephalographic (EEG) frequency bands, and
comprising visible light carrier signals modulated by modulating signals with frequencies that vary non-linearly with time; and
a light source for providing at least one of the one or more stimulation waveforms to a patient as therapeutic visual stimulation;
wherein the at least one of the one or more stimulation waveforms comprises pairs of frequency intervals, the pairs including increasing frequency intervals and decreasing frequency intervals, the frequencies increasing exponentially during the increasing frequency intervals and decreasing exponentially during the decreasing frequency intervals.

2. The device of claim 1, wherein:
the one or more stimulation waveforms comprise a first stimulation waveform corresponding to a low-frequency EEG band and a second stimulation waveform corresponding to a high-frequency EEG band; and
providing the at least one of the one or more stimulation waveforms includes providing the second stimulation waveform before providing the first stimulation waveform.

3. The device of claim 1, wherein:
the one or more stimulation waveforms comprise a first stimulation waveform corresponding to a low-frequency EEG band and a second stimulation waveform corresponding to a high-frequency EEG band; and
providing the at least one of the one or more stimulation waveforms includes providing the first stimulation waveform before providing the second stimulation waveform.

4. The device of claim 1, wherein durations of the pairs vary non-linearly.

5. The device of claim 1, wherein the frequencies increase exponentially from a beginning to an end of each stimulation waveform.

6. The device of claim 1, wherein the frequencies vary exponentially with time.

7. The device of claim 1, wherein durations of the decreasing frequency intervals exceed durations of the increasing frequency intervals.

8. The device of claim 1, wherein durations of the frequency intervals are approximately related by an approximately constant multiple.

9. The device of claim 8, wherein the approximately constant multiple is the golden ratio.

10. The device of claim 1, wherein the EEG frequency bands are selected from a group consisting of delta, theta, alpha, beta 1, beta 2, and gamma EEG frequency bands.

11. A method of therapeutic visual stimulation, comprising:
- measuring, using a portable electroencephalograph, a sympathovagal balance of a patient and contributions from one or more EEG frequency bands to an EEG of the patient;
- generating, using a processor, a train of stimulation waveforms based on an indication of an abnormal physiological state of the patient, one of the stimulation waveforms corresponding to an EEG frequency band and comprising a visible light carrier signal modulated by a modulating signal including frequency intervals comprising:
  - increasing frequency intervals during which a frequency of the modulating signal increases exponentially,
  - decreasing frequency intervals during which the frequency of the modulating signal decreases exponentially, and
  - wherein durations of the increasing frequency intervals and of the decreasing frequency intervals vary and depend on the EEG frequency band corresponding to the one of the stimulation waveforms; and
- providing, using the processor, the train of stimulation waveforms to a light source for generating therapeutic visual stimulation for the patient.

12. The method of claim 11, wherein durations of frequency intervals are approximately related by an approximately constant multiple.

13. The method of claim 12, wherein the approximately constant multiple is the golden ratio.

14. The method of claim 11, wherein the EEG frequency band comprises a delta, theta, alpha, beta 1, beta 2, or gamma EEG frequency band.

15. The method of claim 11, wherein the train of stimulation waveforms is generated remotely from the light source.

16. A non-transitory computer-readable medium comprising instructions that, when executed by a processor of a system, cause the system to perform operations comprising:
- generating a train of stimulation waveforms based on an indication of an abnormal physiological state of a patient, one of the stimulation waveforms corresponding to an EEG frequency band and comprising an visual light signal modulated by a modulating signal including frequency intervals comprising:
  - increasing frequency intervals during which a frequency of the modulating signal increases exponentially,
  - decreasing frequency intervals during which the frequency of the modulating signal decreases exponentially, and
  - wherein durations of the frequency intervals are related by an approximately constant multiple; and
- providing the train of stimulation waveforms to a light source for generating therapeutic visual stimulation for the patient.

17. The non-transitory computer-readable medium of claim 16, wherein the approximately constant multiple is the golden ratio.

18. The non-transitory computer-readable medium of claim 16, wherein the EEG frequency band comprises a delta, theta, alpha, beta 1, beta 2, or gamma EEG frequency band.

19. The non-transitory computer-readable medium of claim 16, wherein:
- the train of stimulation waveforms comprises a first stimulation waveform corresponding to a low-frequency EEG band and a second stimulation waveform corresponding to a high-frequency EEG band; and
- providing the train of stimulation waveforms includes providing the first stimulation waveform before providing the second stimulation waveform.

20. The non-transitory computer-readable medium of claim 16, wherein:
- the train of stimulation waveforms comprises a first stimulation waveform corresponding to a low-frequency EEG band and a second stimulation waveform corresponding to a high-frequency EEG band; and
- providing the train of stimulation waveforms includes providing the second stimulation waveform before providing the first stimulation waveform.

* * * * *